(12) United States Patent
Fushimi et al.

(10) Patent No.: US 7,732,596 B2
(45) Date of Patent: Jun. 8, 2010

(54) FUSED HETEROCYCLE DERIVATIVE, MEDICINAL COMPOSITION CONTAINING THE SAME, AND MEDICINAL USE THEREOF

(75) Inventors: Nobuhiko Fushimi, Azumino (JP); Hideki Fujikura, Azumino (JP); Masayuki Isaji, Azumino (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 130 days.

(21) Appl. No.: 10/591,403
(22) PCT Filed: Mar. 3, 2005
(86) PCT No.: PCT/JP2005/004152
§ 371 (c)(1),
(2), (4) Date: Sep. 1, 2006
(87) PCT Pub. No.: WO2005/085265
PCT Pub. Date: Sep. 15, 2005

(65) Prior Publication Data
US 2007/0197449 A1   Aug. 23, 2007

(30) Foreign Application Priority Data
Mar. 4, 2004   (JP)   ............................. 2004-061429

(51) Int. Cl.
*C07H 7/06* (2006.01)
*C07H 7/04* (2006.01)
*A61K 31/7042* (2006.01)
(52) U.S. Cl. .................. 536/29.2; 536/122; 514/23
(58) Field of Classification Search ................ 536/29.1, 536/122
See application file for complete search history.

(56) References Cited

U.S. PATENT DOCUMENTS

| 5,502,187 | A | | 3/1996 | Ayer et al. |
| 5,582,837 | A | * | 12/1996 | Shell .......................... 424/451 |
| 6,414,126 | B1 | * | 7/2002 | Ellsworth et al. ........... 536/17.2 |
| 7,202,350 | B2 | * | 4/2007 | Imamura et al. ............ 536/1.11 |
| 2002/0013268 | A1 | | 1/2002 | Fryburg et al. |
| 2006/0122126 | A1 | * | 6/2006 | Imamura et al. ............... 514/23 |

FOREIGN PATENT DOCUMENTS

| EP | 1 405859 A1 | 4/2004 |
| EP | 1 609 798 A1 | 12/2005 |
| JP | 8-502721 A | 3/1996 |
| JP | 2001-354568 A | 12/2001 |
| JP | 2002-193948 A | 7/2002 |
| JP | 2003-12686 A | 1/2003 |
| JP | 2004-300102 A | 10/2004 |
| WO | WO 93/20078 | 10/1993 |
| WO | WO 03/000712 A1 | 1/2003 |
| WO | WO 2004080990 A1 * | 9/2004 |
| WO | WO 2004/087727 A1 | 10/2004 |

OTHER PUBLICATIONS

Bedell et al. J. Org. Chem., 1962, 27, p. 2026-2031.*
Handlon A. Expert Opin. Ther. Patents, 2005, 15(11), p. 1531-1540.*
Ellsworth et al. Bioorganic and Medicinal Chemistry Letters, 2008, 18, p. 4770-4773.*
Dudash Jr. et al. Bioorganic and Medicinal Chemistry Letters, 2004, 14, p. 5121-5125.*
Vemula et al. J. Pharma. Exp. Ther., 2008, http://jpet.aspetjournals.org, accessed online at Dec. 17, 2008.*
Definition of prevent, WordNet, http://wordnet.princeton.edu, accessed online Nov. 14, 2007.*
Definition of inhibit, WordNet, http://wordnet.princeton.edu, accessed online Nov. 14, 2007.*
* cited by examiner

*Primary Examiner*—Shaojia Anna Jiang
*Assistant Examiner*—Jonathan S Lau
(74) *Attorney, Agent, or Firm*—Sughrue Mion, PLLC

(57) ABSTRACT

The present invention provides nitrogen-containing fused cyclic derivatives represented by the following general formula or pharmaceutically acceptable salts thereof, or prodrugs thereof, which exhibit an excellent inhibitory activity in human SGLT and are useful as agents for the prevention or treatment of a disease associated with hyperglycemia such as diabetes, postprandial hyperglycemia, impaired glucose tolerance, diabetic complications or obesity, in the formula one of $R^1$ and $R^4$ represents a group represented by the following general formula (S) (in which $R^5$ and $R^6$ represent H, OH, a halogen atom, etc.; Q represents an alkylene group etc.; and ring A represents an aryl group etc.), and the other represents H, OH, an amino group, etc.; $R^2$ and $R^3$ represent H, OH, an amino group, a halogen atom, and an optionally substituted alkyl group, etc.; $A^1$ represents O, S, etc.; $A^2$ represents CH or N; G represents a group represented by the following general formula (G-1) or (G-2) ($E^1$ represents H, F or OH; and $E^2$ represents H, F, a methyl group, etc.), and pharmaceutical compositions comprising the same, and pharmaceutical uses thereof.

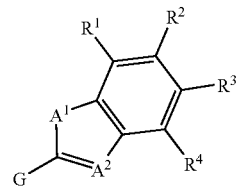

(I)

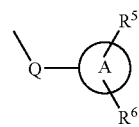

(S)

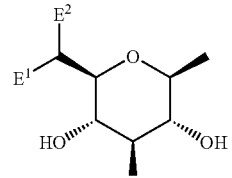

(G-1)

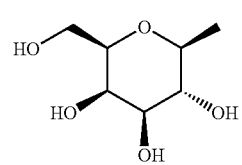

(G-2)

16 Claims, No Drawings

FUSED HETEROCYCLE DERIVATIVE, MEDICINAL COMPOSITION CONTAINING THE SAME, AND MEDICINAL USE THEREOF

TECHNICAL FIELD

The present invention relates to fused heterocyclic derivatives, pharmaceutically acceptable salts thereof or prodrugs thereof, which are useful as medicaments, pharmaceutical compositions comprising the same and pharmaceutical uses thereof.

More particularly, the present invention relates to fused heterocyclic derivatives having an inhibitory activity in human SGLT, pharmaceutically acceptable salts thereof or prodrugs thereof which are useful as agents for the prevention or treatment of a disease associated with hyperglycemia such as diabetes, impaired glucose tolerance, diabetic complications or obesity, pharmaceutical compositions comprising the same and pharmaceutical uses thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. In addition, it has been confirmed by large-scale clinical trial that it is necessary to practice a long-term strict control of blood sugar level so as to prevent patients with diabetes from occurring and advancing diabetic complications by receiving treatment (for example, see the following References 1 and 2). Furthermore, many epidemiologic studies on impaired glucose tolerance and macroangiopathy show that impaired glucose tolerance as the boundary type is also a risk factor in macroangiopathy as well as diabetes. Thus, needs to improve postprandial hyperglycemia have been focused (for example, see the following Reference 3).

In recent years, development of various antidiabetic agents has been progressing with the background of a rapid increase of patients with diabetes. For example, Antidiabetic agents such as biguanides, sulfonylureas, insulin sensitivity enhancers, α-glucosidase inhibitors and the like have been employed. However, biguanides and sulfonylureas show occasionally adverse effects such as lacetic acidosis and hypoglycemia, respectively. Insulin sensitivity enhancers show occasionally adverse effects such as edema, and are concerned for advancing obesity. In addition, α-glucosidase inhibitors, which delay carbohydrate digestion and absorption at the small intestine, are used to improve postprandial hyperglycemia. It has been also reported that acarbose, one of α-glucosidase inhibitors, has an effect of preventing or delaying the incidence of diabetes by applying to patients with impaired glucose tolerance (for example, see the following Reference 4). However, since α-glucosidase inhibitors do not affect elevated glucose levels by ingesting a monosaccharide of glucose (for example, see the following Reference 5), with recently changing compositions of sugars in meals, a wider range of activities inhibiting carbohydrate absorption has been desired.

In recent years, research and development of new type antidiabetic agents have been progressing, which promote urinary glucose excretion and lower blood glucose level by preventing reabsorption of excess glucose at the kidney (for example, see the following Reference 6). In addition, it is reported that SGLT2 (sodium-dependent glucose transporter 2) is present in the S1 segment of the kidney's proximal tubule and participates mainly in reabsorption of glucose filtrated through glomerular (for example, see the following Reference 7). Accordingly, inhibiting a human SGLT2 activity prevents reabsorption of excess glucose at the kidney, subsequently promotes excreting excess glucose though the urine, and normalizes blood glucose level. In addition, since such agents for promoting the excretion of urinary glucose excrete excess glucose though the urine and consequently the glucose accumulation in the body is decreased, they are also expected to have a preventing or alleviating effect on obesity and a diuretic effect. Furthermore, the agents are considered to be useful for various related diseases which occur accompanying the progress of diabetes or obesity due to hyperglycemia.

Furthermore, it has been known that SGLT1, sodium-dependent glucose transporter 1, exists in the small intestine which controls carbohydrate absorption. It has been also reported that insufficiency of glucose and galactose absorption arises inpatients with dysfunction due to congenital abnormalities of human SGLT1 (for example, see the following References 8-10). In addition, it has been confirmed that SGLT1 is involved in glucose and galactose absorption (for example, see the following References 11 and 12). Furthermore, it is confirmed that mRNA and protein of SGLT1 increase and absorption of glucoses are accelerated in OLETF rats and rats with streptozotocin-induced diabetic symptoms (for example, see the following References 13 and 14). Generally in patients with diabetes, carbohydrate digestion and absorption are increased. For example, it is confirmed that mRNA and protein of SGLT1 are highly increased in the human small intestine (for example, see the following Reference 15). Therefore, blocking a human SGLT1 activity inhibits absorption of carbohydrates such as glucose at the small intestine, subsequently can prevent increase of blood sugar level. Especially, it is considered that delaying glucose absorption based on the above mentioned mechanism is effective to normalize postprandial hyperglycemia.

Therefore, fast development of antidiabetic agents with novel action mechanism, which have an inhibitory activity in human SGLT, has been desired to improve or solve the above-mentioned problems.

Fused heterocyclic derivatives provided in the present invention are entirely novel compounds. It has not ever been reported that these derivatives have an inhibitory activities in SGLT1 and/or SGLT2 and inhibit absorption of glucose and galactose at the small intestine, or are useful as agents to inhibit reabsorption of excess glucose at the kidney.

Reference 1: The Diabetes Control and Complications Trial Research Group, N. Engl. J. Med., 1993.9, Vol. 329, No. 14, pp. 977-986;

Reference 2: UK Prospective Diabetes Study Group, Lancet, 1998.9, Vol. 352, No. 9131, pp. 837-853;

Reference 3: Makoto TOMINAGA, Endocrinology & Diabetology, 2001.11, Vol. 13, No. 5, pp. 534-542;

Reference 4: Jean-Louis Chiassonand 5 persons, Lancet, 2002.6, Vol. 359, No. 9323, pp. 2072-2077;

Reference 5: Hiroyuki ODAKA and 3 persons, Journal of Japanese Society of Nutrition and Food Science, 1992, Vol. 45, p. 27;

Reference 6: Luciano Rossetti and 4 persons, J. Clin. Invest., 1987.5, Vol. 79, pp. 1510-1515;

Reference 7: Yoshikatsu Kanai and 4 persons, J. Clin. Invest., 1994.1, Vol. 93, pp. 397-404;

Reference 8: Tadao BABA and 1 person, Supplementary volume of Nippon Rinsho, Ryoikibetsu Shokogun, 1998, No. 19, pp. 552-554;

Reference 9: Michihiro KASAHARA and 2 persons, Saishin Igaku, 1996.1, Vol. 51, No. 1, pp. 84-90;
Reference 10: Tomofusa TSUCHIYA and 1 person, Nippon Rinsho, 1997.8, Vol. 55, No. 8, pp. 2131-2139;
Reference 11: Yoshikatsu KANAI, Kidney and Dialysis, 1998.12, Vol. 45, extra edition, pp. 232-237;
Reference 12: E. Turk and 4 persons, Nature, 1991.3, Vol. 350, pp. 354-356;
Reference 13: Y. Fujita and 5 persons, Diabetologia, 1998, Vol. 41, pp. 1459-1466;
Reference 14: J. Dyer and 5 persons, Biochemical Society Transactions, 1997, Vol. 25, p. 479S;
Reference 15: J. Dyer and 4 persons, American Journal of Physiology, 2002.2, Vol. 282, No. 2, pp. G241-G248

DISCLOSURE OF THE INVENTION

The present inventors have studied earnestly to find compounds having an inhibitory activity in human SGLT. As a result, it was found that certain fused heterocyclic derivatives represented by the following general formula (I) show an inhibitory activity in human SGLT1 and/or SGLT2 and are excellent agents having inhibitory activity in increase of blood glucose level or lowering blood glucose level as shown below, thereby forming the basis of the present invention.

The present invention is to provide novel compounds which show an inhibitory activity in human SGLT, pharmaceutical compositions comprising the same and pharmaceutical uses thereof.

This is, the present invention relates to

[1] a fused heterocyclic derivative represented by the following general formula (I):

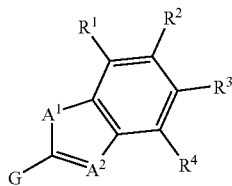

(I)

wherein
one of $R^1$ and $R^4$ represents a group represented by the general formula:

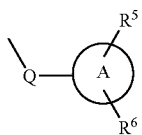

(S)

[in the formula $R^5$ and $R^6$ independently represent a hydrogen atom, a hydroxy group, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{2-6}$ alkenylthio group, a halo($C_{1-6}$ alkyl) group, a halo($C_{1-6}$ alkoxy) group, a halo($C_{1-6}$ alkylthio) group, a hydroxy($C_{1-6}$ alkyl) group, a hydroxy($C_{2-6}$ alkenyl) group, a hydroxy($C_{1-6}$ alkoxy) group, a hydroxy($C_{1-6}$ alkylthio) group, a carboxy group, a carboxy($C_{1-6}$ alkyl) group, a carboxy($C_{2-6}$ alkenyl) group, a carboxy($C_{1-6}$ alkoxy) group, a carboxy($C_{1-6}$ alkylthio) group, a $C_{2-7}$ alkoxycarbonyl group, a $C_{2-7}$ alkoxycarbonyl($C_{1-6}$ alkyl) group, a $C_{2-7}$ alkoxycarbonyl($C_{2-6}$ alkenyl) group, a $C_{2-7}$ alkoxycarbonyl($C_{1-6}$ alkoxy) group, a $C_{2-7}$ alkoxycarbonyl($C_{1-6}$ alkylthio) group, a $C_{1-6}$ alkylsulfinyl group, a $C_{1-6}$ alkylsulfonyl group, —U—V—W—N($R^7$)—Z, or any of the following substituents (i) to (xxviii) which may have 1 to 3 substitutents selected from the following substitutent group α on the ring;

(i) a $C_{6-10}$ aryl group, (ii) $C_{6-10}$ aryl-O—, (iii) $C_{6-10}$ aryl-S—, (iv) a $C_{6-10}$ aryl($C_{1-6}$ alkyl) group, (v) a $C_{6-10}$ aryl($C_{1-6}$ alkoxy) group, (vi) a $C_{6-10}$ aryl($C_{1-6}$ alkylthio) group, (vii) a heteroaryl group, (viii) heteroaryl-O—, (ix) heteroaryl-S—, (x) a heteroaryl($C_{1-6}$ alkyl) group, (xi) a heteroaryl($C_{1-6}$ alkoxy) group, (xii) a heteroaryl($C_{1-6}$ alkylthio) group, (xiii) a $C_{3-7}$ cycloalkyl group, (xiv) $C_{3-7}$ cycloalkyl-O—, (xv) $C_{3-7}$ cycloalkyl-S—, (xvi) a $C_{3-7}$ cycloalkyl($C_{1-6}$ alkyl) group, (xvii) a $C_{3-7}$ cycloalkyl($C_{1-6}$ alkoxy) group, (xviii) a $C_{3-7}$ cycloalkyl($C_{1-6}$ alkylthio) group, (xix) a heterocycloalkyl group, (xx) heterocycloalkyl-O—, (xxi) heterocycloalkyl-S—, (xxii) a heterocycloalkyl($C_{1-6}$ alkyl) group, (xxiii) a heterocycloalkyl($C_{1-6}$ alkoxy) group, (xxiv) a heterocycloalkyl($C_{1-6}$ alkylthio) group, (xxv) an aromatic cyclic amino group, (xxvi) an aromatic cyclic amino($C_{1-6}$ alkyl) group or (xxvii) an aromatic cyclic amino($C_{1-6}$ alkoxy) group, (xxviii) an aromatic cyclic amino($C_{1-6}$ alkylthio) group, J represents a $C_{1-6}$ alkylene group which may have a hydroxy group, or a $C_{2-6}$ alkenylene group;

U represents —O—, —S— or a single bond and with the proviso that at least one of V and W is not a single bond when U is —O— or —S—);

V represents a $C_{1-6}$ alkylene group which may have a hydroxy group, a $C_{2-6}$ alkenylene group or a single bond;

W represents —CO—, —SO$_2$—, —C(=NH)— or a single bond;

Z independently represents a hydrogen atom, a $C_{2-7}$ alkoxycarbonyl group, a $C_{6-10}$ aryl($C_{2-7}$ alkoxycarbonyl) group, a formyl group, —$R^A$, —COR$^B$, —SO$_2$R$^B$, —CON(R$^C$)R$^D$, —CSN(R$^C$)R$^D$, —SO$_2$NHR$^A$ or —C(=NR$^E$)N(R$^F$)R$^G$;

$R^7$, $R^A$, $R^C$ and $R^D$ independently represent a hydrogen atom, a $C_{1-6}$ alkyl group which may have 1 to 5 substitutents selected from the following substitutent group β, or any of the following substitutents (xxix) to (xxxii) which may have 1 to 3 substitutents selected from the following substitutent group α;

(xxix) a $C_{6-10}$ aryl group, (xxx) a heteroaryl group, (xxxi) a $C_{3-7}$ cycloalkyl group or (xxxii) a heterocycloalkyl group or Z and $R^7$ bind together with the neighboring nitrogen atom to form an aliphatic cyclic amino group which may have 1 to 3 substitutents selected from the following substitutent group α;

or $R^C$ and $R^D$ bind together with the neighboring nitrogen atom to form an aliphatic cyclic amino group which may have 1 to 3 substitutents selected from the following substitutent group α;

$R^B$ represents a $C_{2-7}$ alkoxycarbonyl group, a $C_{1-6}$ alkylsulfonylamino group, a $C_{6-10}$ arylsulfonylamino group, a $C_{1-6}$ alkyl group which may have 1 to 5 substitutents selected from the following substitutent group β, or any of the following substitutents (xxxiii) to (xxxvi) which may have 1 to 3 substitutents selected from the following substitutent group α;

(xxxiii) a $C_{6-10}$ aryl group, (xxxiv) a heteroaryl group, (xxxv) a $C_{3-7}$ cycloalkyl group or (xxxvi) a heterocycloalkyl group, $R^E$, $R^F$ and $R^G$ independently represent a hydrogen atom, a cyano group, a carbamoyl group, a $C_{2-7}$ acyl group, a $C_{2-7}$ alkoxycarbonyl group, a $C_{6-10}$ aryl($C_{2-7}$ alkoxycarbonyl)

group, a nitro group, a $C_{1-6}$ alkylsulfonyl group, a sulfamide group, a carbamimidoyl group, or a $C_{1-6}$ alkyl group which may have 1 to 5 substituents selected from the following substituent group β;

or $R^E$ and $R^F$ bind together to form an ethylene group;

or $R^E$ and $R^G$ bind together with the neighboring nitrogen atom to form an aliphatic cyclic amino group which may have any substituent selected from the following substituent group α;

Q represents —$C_{1-6}$ alkylene-, —$C_{2-6}$ alkenylene-, —$C_{2-6}$ alkynylene-, —$C_{1-6}$ alkylene-O—, —$C_{1-6}$ alkylene-S—, —O—$C_{1-6}$ alkylene-, —S—$C_{1-6}$ alkylene-, —$C_{1-6}$ alkylene-O—$C_{1-6}$ alkylene-, —$C_{1-6}$ alkylene-S—$C_{1-6}$ alkylene-, —CON($R^8$)—, —N($R^8$)CO—, —$C_{1-6}$ alkylene-CON($R^8$)— or —CON($R^8$)—$C_{1-6}$ alkylene-;

$R^8$ represents a hydrogen atom or a $C_{1-6}$ alkyl group;

ring A represents a $C_{6-10}$ aryl group or a heteroaryl group] and the other of $R^1$ and $R^4$ represents a hydrogen atom, a hydroxy group, an amino group, a halogen atom, a $C_{1-6}$ alkyl group, a $C_{1-6}$ alkoxy group, a cyano group, a carboxy group, a $C_{2-7}$ alkoxycarbonyl group, a carbamoyl group, a mono or di($C_{1-6}$ alkyl)amino group, a halo($C_{1-6}$ alkyl) group, a hydroxy($C_{1-6}$ alkyl) group, a cyano($C_{1-6}$ alkyl) group, a carboxy($C_{1-6}$ alkyl) group, a $C_{2-7}$ alkoxycarbonyl($C_{1-6}$ alkyl) group, a carbamoyl($C_{1-6}$ alkyl) group, an amino($C_{1-6}$ alkyl) group, a mono or di($C_{1-6}$ alkyl)amino($C_{1-6}$ alkyl) group, a halo($C_{1-6}$ alkoxy) group, a hydroxy($C_{1-6}$ alkoxy) group, a carboxy($C_{1-6}$ alkoxy) group, a $C_{2-7}$ alkoxycarbonyl($C_{1-6}$ alkoxy) group, a carbamoyl($C_{1-6}$ alkoxy) group, an amino ($C_{1-6}$ alkoxy) group, a mono or di($C_{1-6}$ alkyl)amino($C_{1-6}$ alkoxy) group, a $C_{3-7}$ cycloalkyl group, a $C_{3-7}$ cycloalkyloxy group, a $C_{3-7}$ cycloalkyl($C_{1-6}$ alkyl) group, or $C_{3-7}$ cycloalkyl($C_{1-6}$ alkoxy) group;

$R^2$ and $R^3$ independently represent a hydrogen atom, a hydroxy group, an amino group, a halogen atom, a $C_{1-6}$ alkyl group, a $C_{1-6}$ alkoxy group, a cyano group, a carboxy group, a $C_{2-7}$ alkoxycarbonyl group, a carbamoyl group, a mono or di($C_{1-6}$ alkyl)amino group, a halo($C_{1-6}$ alkyl) group, a hydroxy($C_{1-6}$ alkyl) group, a cyano($C_{1-6}$ alkyl) group, a carboxy($C_{1-6}$ alkyl) group, a $C_{2-7}$ alkoxycarbonyl($C_{1-6}$ alkyl) group, a carbamoyl($C_{1-6}$ alkyl) group, an amino($C_{1-6}$ alkyl) group, a mono or di($C_{1-6}$ alkyl)amino($C_{1-6}$ alkyl) group, a halo($C_{1-6}$ alkoxy) group, a hydroxy($C_{1-6}$ alkoxy) group, a carboxy($C_{1-6}$ alkoxy) group, a $C_{2-7}$ alkoxycarbonyl($C_{1-6}$ alkoxy) group, a carbamoyl($C_{1-6}$ alkoxy) group, an amino($C_{1-6}$ alkoxy) group, a mono or di($C_{1-6}$ alkyl)amino($C_{1-6}$ alkoxy) group, a $C_{3-7}$ cycloalkyl group, a $C_{3-7}$ cycloalkyloxy group, a $C_{3-7}$ cycloalkyl($C_{1-6}$ alkyl) group, or $C_{3-7}$ cycloalkyl($C_{1-6}$ alkoxy) group;

$A^1$ represents O, S or $NR^9$;

$A^2$ represents CH or N;

$R^9$ represents a hydrogen atom or a $C_{1-6}$ alkyl group;

G represents a group represented by a formula:

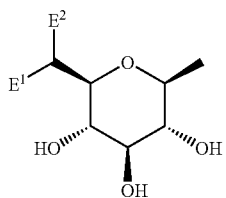

(G-1)

or a formula:

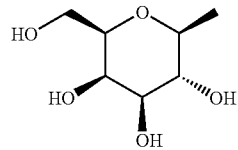

(G-2)

$E^1$ represents a hydrogen atom, a fluorine atom or a hydroxy group;

$E^2$ represents a hydrogen atom, a fluorine atom, a methyl group or a hydroxymethyl group;

[substituent group α]

a halogen atom, a hydroxy group, an amino group, a $C_{1-6}$ alkyl group, a $C_{1-6}$alkoxy group, a halo($C_{1-6}$ alkyl) group, a halo ($C_{1-6}$ alkoxy)group, a hydroxy($C_{1-6}$ alkyl) group, a $C_{2-7}$ alkoxycarbonyl($C_{1-6}$ alkyl) group, a hydroxy($C_{1-6}$alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)]amino group, a $C_{1-6}$ alkylsulfonyl group, a $C_{1-6}$ alkylsulfonylamino group, a $C_{1-6}$ alkylsulfonylamino ($C_{1-6}$ alkyl) group, a carboxy group, a $C_{2-7}$ alkoxycarbonyl group, a sulfamoyl group and —CON($R^H$)$R^I$

[substituent group β]

a halogen atom, a hydroxy group, an amino group, a $C_{1-6}$ alkoxy group, a $C_{1-6}$ alkylthio group, a halo($C_{1-6}$ alkoxy) group, a halo($C_{1-6}$ alkylthio) group, a hydroxy($C_{1-6}$ alkoxy) group, a hydroxy($C_{1-6}$ alkylthio) group, an amino($C_{1-6}$ alkoxy) group, an amino($C_{1-6}$ alkylthio) group, a mono or di($C_{1-6}$ alkyl)amino group, a mono or di[hydroxy($C_{1-6}$ alkyl)] amino group, an ureido group, a sulfamide group, a mono or di($C_{1-6}$ alkyl)ureido group, a mono or di[hydroxy($C_{1-6}$ alkyl)] ureido group, a mono or di($C_{1-6}$ alkyl)sulfamide group, a mono or di[hydroxy($C_{1-6}$ alkyl)]-sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl ($C_{1-6}$ alkylsulfonylamino) group, a carboxy group, a $C_{2-7}$ alkoxycarbonyl group, —CON($R^H$)$R^I$, and any of the following substituents (xxxvii) to (xxxxviii) which may have 1 to 3 substituents selected from the above substituent group α;

(xxxvii) a $C_{6-10}$ aryl group, (xxxviii) $C_{6-10}$ aryl-O—, (xxxix) a $C_{6-10}$ aryl($C_{1-6}$ alkoxy) group, (xxxx) a $C_{6-10}$ aryl ($C_{1-6}$ alkylthio) group, (xxxxi) a heteroaryl group, (xxxxii) heteroaryl-O—, (xxxxiii) a $C_{3-7}$ cycloalkyl group, (xxxxiv) $C_{3-7}$ cycloalkyl-O—, (xxxxv) a heterocycloalkyl group, (xxxxvi) heterocycloalkyl-O—, (xxxxvii) an aliphatic cyclic amino group or (xxxxviii) an aromatic cyclic amino group $R^H$ and $R^I$ independently represent a hydrogen atom or a $C_{1-6}$ alkyl group which may have 1 to 3 substituents selected from the following substituent group γ;

or both of $R^H$ and $R^I$ bind together with the neighboring nitrogen atom to form an aliphatic cyclic amino group which may have 1 to 3 substituents selected from the following substituent group δ;

[substituent group γ]

a halogen atom, a hydroxy group, an amino group, a $C_{1-6}$ alkoxy group, a halo($C_{1-6}$ alkoxy) group, a hydroxy($C_{1-6}$ alkoxy) group, an amino($C_{1-6}$alkoxy) group, a mono or di($C_{1-6}$ alkyl)amino group, a mono or di[hydroxy($C_{1-6}$ alkyl)] amino group, an ureido group, a sulfamide group, a mono or di($C_{1-6}$ alkyl)ureido group, a mono or di[hydroxy($C_{1-6}$ alkyl)] ureido group, a mono or di($C_{1-6}$ alkyl)sulfamide group, a mono or di[hydroxy($C_{1-6}$ alkyl)]-sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl ($C_{1-6}$ alkylsulfonylamino) group, a carboxy group, a $C_{2-7}$ alkoxycarbonyl group, a sulfamoyl group and —CON($R^J$)$R^K$

[substitutent group δ]

a halogen atom, a hydroxy group, an amino group, a $C_{1-6}$ alkyl group, a $C_{1-6}$ alkoxy group, a halo($C_{1-6}$ alkyl) group, a halo ($C_{1-6}$ alkoxy) group, a hydroxy($C_{1-6}$ alkyl) group, a $C_{2-7}$ alkoxycarbonyl($C_{1-6}$ alkyl) group, a hydroxy($C_{1-6}$alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)]amino group, a $C_{1-6}$ alkylsulfonyl group, a $C_{1-6}$ alkylsulfonylamino group, a $C_{1-6}$ alkylsulfonylamino ($C_{1-6}$ alkyl) group, a carboxy group, a $C_{2-7}$ alkoxycarbonyl group, a sulfamoyl group and —CON($R^J$)$R^K$ $R^J$ and $R^K$ independently represent a hydrogen atom or a $C_{1-6}$ alkyl group which may have any 1 to 3 substitutents selected from a hydroxy group, an amino group, a mono or di($C_{1-6}$ alkyl)amino group, a $C_{2-7}$ alkoxycarbonyl group and a carbamoyl group;

or both of $R^J$ and $R^K$ bind together with the neighboring nitrogen atom to form an aliphatic cyclic amino group which may have any 1 to 3 substitutents selected from a hydroxy group, an amino group, a mono or di($C_{1-6}$ alkyl)amino group, a $C_{1-6}$ alkyl group, a hydroxy($C_{1-6}$ alkyl) group, a $C_{2-7}$ alkoxycarbonyl group, a $C_{2-7}$ alkoxycarbonyl($C_{1-6}$ alkyl) group and a carbamoyl group, or a pharmaceutically acceptable salt thereof, or a prodrug thereof;

[2] a fused heterocyclic derivative as described in the above [1], wherein Q represents a methylene group, an ethylene group, —OCH$_2$—, —CH$_2$O—, —SCH$_2$— or —CH$_2$S—, or a pharmaceutically acceptable salt thereof, or a prodrug thereof;

[3] a fused heterocyclic derivative as described in the above [2], wherein Q represents an ethylene group, or a pharmaceutically acceptable salt thereof, or a prodrug thereof;

[4] a fused heterocyclic derivative as described in the above [2], wherein Q represents a methylene group, or a pharmaceutically acceptable salt thereof, or a prodrug thereof;

[5] a fused heterocyclic derivative as described in the above [1], wherein $R^5$ and $R^6$ independently represent a hydrogen atom, a hydroxy group, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{2-6}$ alkenylthio group, a halo($C_{1-6}$ alkyl) group, a halo($C_{1-6}$ alkoxy) group, a halo($C_{1-6}$ alkylthio) group, a hydroxy($C_{1-6}$ alkyl) group, a hydroxy($C_{2-6}$ alkenyl) group, a hydroxy($C_{1-6}$ alkoxy) group or a hydroxy($C_{1-6}$ alkylthio) group, or a pharmaceutically acceptable salt thereof, or a prodrug thereof;

[6] a fused heterocyclic derivative as described in any one of the above [1] to [5], wherein the ring A represents a benzene ring or a pyridine ring, or a pharmaceutically acceptable salt thereof, or a prodrug thereof;

[7] a fused heterocyclic derivative as described in any one of the above [1] to [6], wherein G represents a group represented by the formula:

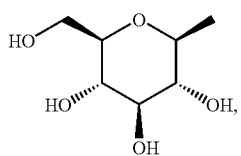

or a pharmaceutically acceptable salt thereof, or a prodrug thereof;

[8] a pharmaceutical composition comprising as an active ingredient a fused heterocyclic derivative as described in any one of the above [1] to [7], or a pharmaceutically acceptable salt thereof, or a prodrug thereof;

[9] a human SGLT inhibitor comprising as an active ingredient a fused heterocyclic derivative as described in any one of the above [1] to [7], or a pharmaceutically acceptable salt thereof, or a prodrug thereof;

[10] a human SGLT inhibitor as described in the above [9], wherein the SGLT is SGLT1 and/or SGLT2;

[11] a human SGLT inhibitor as described in the above [9], which is an agent for the inhibition of postprandial hyperglycemia;

[12] a human SGLT inhibitor as described in the above [9], which is an agent for the prevention or treatment of a disease associated with hyperglycemia;

[13] a human SGLT inhibitor as described in the above [12], wherein the disease associated with hyperglycemia is a disease selected from the group consisting of diabetes, impaired glucose tolerance, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia and gout;

[14] a human SGLT inhibitor as described in the above [9], which is an agent for the inhibition of advancing impaired glucose tolerance into diabetes in a subject;

[15] a pharmaceutical composition as described in the above [8], wherein the dosage form is sustained release formulation;

[16] a human SGLT inhibitor as described in the above [9], wherein the dosage form is sustained release formulation;

[17] a method for the inhibition of postprandial hyperglycemia, which comprises administering an effective amount of a fused heterocyclic derivative as described in any one of the above [1] to [7], or a pharmaceutically acceptable salt thereof, or a prodrug thereof;

[18] a method for the prevention or treatment of a disease associated with hyperglycemia, which comprises administering an effective amount of a fused heterocyclic derivative as described in any one of the above [1] to [7], or a pharmaceutically acceptable salt thereof, or a prodrug thereof;

[19] a method for the prevention or treatment as described in the above [18], wherein the disease associated with hyperglycemia is a disease selected from the group consisting of diabetes, impaired glucose tolerance, diabetic complications, obesity, hyperinsulinemia, hyperlipidemia, hyper-cholesterolemia, hypertriglyceridemia, lipid metabolism disorder, atherosclerosis, hypertension, congestive heart failure, edema, hyperuricemia and gout;

[20] a method for the inhibition of advancing impaired glucose tolerance into diabetes in a subject, which comprises administering an effective amount of a fused heterocyclic derivative as described in any one of the above [1] to [7], or a pharmaceutically acceptable salt thereof, or a prodrug thereof;

[21] a use of a fused heterocyclic derivative as described in any one of the above [1] to [7], or a pharmaceutically acceptable salt thereof, or a prodrug thereof for the manufacture of a pharmaceutical composition for the inhibition of postprandial hyperglycemia;

[22] a use of a fused heterocyclic derivative as described in any one of the above [1] to [7], or a pharmaceutically acceptable salt thereof, or a prodrug thereof for the manufacture of a pharmaceutical composition for the prevention or treatment of a disease associated with hyperglycemia;

[23] a use as described in the above [22], wherein the disease associated with hyperglycemia is a disease selected from the group consisting of diabetes, impaired glucose tolerance, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia and gout;

[24] a use of a fused heterocyclic derivative as described in any one of the above [1] to [7], or a pharmaceutically acceptable salt thereof, or a prodrug thereof for the manufacture of a pharmaceutical composition for the inhibition of advancing impaired glucose tolerance into diabetes in a subject;

[25] a pharmaceutical composition as described in the above [8], which comprises combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[26] a human SGLT inhibitor as described in the above [9], which comprises combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[27] a method for the inhibition of postprandial hyperglycemia as described in the above [17], which comprises administering in combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[28] a method for the prevention or treatment of a disease associated with hyperglycemia as described in the above [18], which comprises administering in combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, cathartics, a hydroxymethylglutaryl coenzyme A reductase inhibitor, a fibrate, a $\beta_3$-adrenoceptor agonist, an acyl-coenzyme cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[29] a method for the inhibition of advancing impaired glucose tolerance into diabetes in a subject as described in the above [19], which comprises administering in combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[30] a use of (A) a fused heterocyclic derivative as described in anyone of the above [1] to [7], or a pharmaceutically acceptable salt thereof, or a prodrug thereof and (B) at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the inhibition of postprandial hyperglycemia;

[31] a use of (A) a fused heterocyclic derivative as described in any one of the above [1] to [7], or a pharmaceutically acceptable salt thereof, or a prodrug thereof and (B) at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the prevention or treatment of a disease associated with hyperglycemia;

[32] a use of (A) a fused heterocyclic derivative as described in any one of the above [1] to [7], or a pharmaceutically acceptable salt thereof, or a prodrug thereof and (B) at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the inhibition of advancing impaired glucose tolerance into diabetes in a subject; and the like.

In the present invention, the term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "$C_{1-6}$ alkylene group" or "—$C_{1-6}$ alkylene-" means a straight-chained or branched alkylene group having 1 to 6 carbon atoms such as a methylene group, an ethylene group, a trimethylene group, a tetramethylene group, a propylene group, a 1,1-dimethylethylene group or the like; and the term "$C_{1-4}$ alkylene group" or "—$C_{1-4}$ alkylene-" means a straight-chained or branched alkylene group having 1 to 4 carbon atoms such as a methylene group, an ethylene group, a trimethylene group, a tetramethylene group, a propylene group, a 1,1-dimethylethylene group or the like. The term "hydroxy($C_{1-6}$ alkyl) group" means the above $C_{1-6}$ alkyl group substituted by a hydroxy group; the term "dihydroxy($C_{1-6}$ alkyl) group" means the above $C_{1-6}$ alkyl group substituted by two hydroxy groups such as a 2,3-dihydroxypropyl group, a 1,3-dihyroxy-2-propyl group or the like; the term "amino($C_{1-6}$ alkyl) group" means the above $C_{1-6}$ alkyl group substituted by an amino group such as an aminomethyl group, a 2-aminoethyl group or the like; the term "carbamoyl($C_{1-6}$ alkyl) group" means the above $C_{1-6}$ alkyl group substituted by a carbamoyl group; and the term "carboxy($C_{1-6}$ alkyl) group" means the above $C_{1-6}$ alkyl group substituted by a carboxy group.

The term "$C_{1-6}$ alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; the term "hydroxy($C_{1-6}$ alkoxy) group" means the above $C_{1-6}$ alkoxy group substituted by a hydroxy group; the term "carboxy($C_{1-6}$ alkoxy) group" means the above $C_{1-6}$ alkoxy group substituted by a carboxy group; the term "carbamoyl($C_{1-6}$alkoxy) group" means the above $C_{1-6}$ alkoxy group substituted by a carbamoyl group; and the term "amino($C_{1-6}$ alkoxy) group" means the above $C_{1-6}$ alkoxy group substituted by an amino group. The term "$C_{1-6}$ alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like; the term "hydroxy($C_{1-6}$ alkylthio) group" means the above $C_{1-6}$ alkylthio group substituted by a hydroxy group; the term "carboxy($C_{1-6}$ alkylthio) group" means the above $C_{1-6}$ alkylthio group substituted by a carboxy group; and the term "amino($C_{1-6}$ alkylthio) group" means the above $C_{1-6}$ alkylthio group substituted by an amino group.

The term "$C_{2-6}$ alkenyl group" means a straight-chained or branched alkenyl group having 2 to 6 carbon atoms such as a vinyl group, an allyl group, a 1-propenyl group, an isopropenyl group, a 1-butenyl group, a 2-butenyl group, a 2-methylallyl group or the like; the term "$C_{2-6}$ alkenylene group" or "—$C_{2-6}$ alkenylene-" means a straight-chained or branched alkenylene group having 2 to 6 carbon atoms such as a vinylene group, a propenylene group or the like; the term "$C_{2-4}$ alkenylene group" means a straight-chained or branched alkenylene group having 2 to 4 carbon atoms such as a vinylene group, a propenylene group or the like; the term "hydroxy($C_{2-6}$ alkenyl) group" means the above $C_{2-6}$ alkenyl group substituted by a hydroxy group; the term "carboxy ($C_{2-6}$ alkenyl) group" means the above $C_{2-6}$ alkenyl group substituted by a carboxy group; the term "cyano($C_{2-6}$ alkenyl) group" means the above $C_{2-6}$ alkenyl group substituted by a cyano group; the term "$C_{2-6}$ alkenyloxy group" means a straight-chained or branched alkenyloxy group having 2 to 6 carbon atoms such as a vinyloxy group, an allyloxy group, a 1-propenyloxy group, an isopropenyloxy group, a 1-butenyloxy group, a 2-butenyloxy group, a 2-methylallyloxy group or the like; the term "$C_{2-6}$ alkenylthio group" means a straight-chained or branched alkenylthio group having 2 to 6 carbon atoms such as a vinylthio group, an allylthio group, a 1-propenylthio group, an isopropenylthio group, a 1-butenylthio group, a 2-butenylthio group, a 2-methylallylthio group or the like; the term "$C_{2-6}$ alkynyl group" means a straight-chained or branched alkynyl group having 2 to 6 carbon atoms such as an ethynyl group, a 2-propynyl group or the like; and the term "—$C_{2-4}$ alkynylene-" means a straight-chained ot branched alkynylene group having 2 to 4 carbon atoms such as an ethynylene group, a propynylene group or the like.

The term "mono or di($C_{1-6}$ alkyl)amino group" means an amino group mono-substituted by the above $C_{1-6}$ alkyl group or di-substituted by the same or different $C_{1-6}$ alkyl groups as defined above; the term "mono or di($C_{1-6}$ alkyl)amino($C_{1-6}$ alkyl) group" means the above $C_{1-6}$ alkyl group substituted by the above mono or di($C_{1-6}$ alkyl)amino group; the term "mono or di($C_{1-6}$ alkyl)amino($C_{1-6}$alkoxy) group" means the above $C_{1-6}$alkoxy group substituted by the above mono or di($C_{1-6}$ alkyl)amino group; the term "mono or di[hydroxy ($C_{1-6}$ alkyl)] amino group" means an amino group mono-substituted by the above hydroxy($C_{1-6}$ alkyl) group or di-substituted by any of the above hydroxy($C_{1-6}$ alkyl) groups; the term "mono or di($C_{1-6}$ alkyl)ureido group" means an ureido group mono-substituted by the above $C_{1-6}$ alkyl group or di-substituted by any of the above $C_{1-6}$ alkyl groups; the term "mono or di[hydroxy($C_{1-6}$ alkyl)]ureido group" means an ureido group mono-substituted by the above hydroxy($C_{1-6}$ alkyl) group or di-substituted by any of the above hydroxy ($C_{1-6}$ alkyl) groups; the term "mono or di($C_{1-6}$ alkyl)sulfamide group" means a sulfamide group mono-substituted by the above $C_{1-6}$ alkyl group or di-substituted by any of the above $C_{1-6}$ alkyl groups; the term "mono or di[hydroxy($C_{1-6}$ alkyl)]sulfamide group" means a sulfamide group mono-substituted by the above hydroxy($C_{1-6}$ alkyl) group or di-substituted by any of the above hydroxy($C_{1-6}$ alkyl) groups; the term "$C_{2-7}$ acyl group" means a straight-chained or branched acyl group having 2 to 7 carbon atoms such as an acetyl group, a propionyl group, a butyryl group, an isobutyryl group, a valeryl group, a pivaloyl group, a hexanoyl group or the like; the term "$C_{2-7}$ acylamino group" means an amino group substituted by the above $C_{2-7}$ acyl group; and the term "amino ($C_{2-7}$ acylamino) group" means the above $C_{2-7}$ acylamino group substituted by an amino group, such as a 2-aminoacetylamino group, a 3-aminopropionylamino group or the like. The term "$C_{1-6}$ alkylsulfinyl group" means a straight-chained or branched alkylsulfinyl group having 1 to 6 carbon atoms such as a methylsulfinyl group, an ethylsulfinyl group or the like; the term "$C_{1-6}$ alkylsulfonyl group" means a straight-chained or branched alkylsulfonyl group having 1 to 6 carbon atoms such as a methanesulfonyl group, an ethanesulfonyl group or the like; the term "$C_{1-6}$ alkylsulfonylamino group" means an amino group substituted by the above $C_{1-6}$ alkylsulfonyl group; the term "carbamoyl($C_{1-6}$ alkylsulfonylamino) group" means the above $C_{1-6}$ alkylsulfonylamino group substituted by a carbamoyl group, such as a carbamoylmethanesulfonylamino group or the like; and the term "$C_{1-6}$ alkylsulfonylamino($C_{1-6}$ alkyl) group" means the above $C_{1-6}$ alkyl group substituted by the above $C_{1-6}$ alkylsulfonylamino group.

The term "halogen atom" means a fluorine atom, a chlorine atom, a bromine atom or an iodine atom; the term "halo($C_{1-6}$ alkyl) group" means the above $C_{1-6}$ alkyl group substituted by any 1 to 3 halogen atoms as defined above; the term "halo ($C_{1-6}$ alkoxy) group" means the above $C_{1-6}$ alkoxy group substituted by any 1 to 3 halogen atoms as defined above; and the term "halo($C_{1-6}$ alkylthio) group" means the above $C_{1-6}$ alkylthio group substituted by any 1 to 3 halogen atoms as defined above. The term "$C_{2-7}$ alkoxycarbonyl group" means a straight-chained or branched alkoxycarbonyl group having 2 to 7 carbon atoms such as a methoxycarbonyl group, an ethoxycarbonyl group, a propoxycarbonyl group, an isopropoxycarbonyl group, a butoxycarbonyl group, an isobutyloxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like; the term "$C_{2-7}$ alkoxycarbonyl($C_{1-6}$ alkyl) group" means the above $C_{1-6}$ alkyl group substituted by the above $C_{2-7}$ alkoxycarbonyl group; the term "$C_{2-7}$ alkoxycarbonyl($C_{1-6}$alkoxy) group" means the above $C_{1-6}$ alkoxy group substituted by the above $C_{2-7}$ alkoxycarbonyl group; the term "$C_{2-7}$ alkoxycarbonyl($C_{1-6}$ alkylthio) group" means the above $C_{1-6}$ alkylthio group substituted by the above $C_{2-7}$ alkoxycarbonyl group; and the term "$C_{2-7}$ alkoxycarbonyl($C_{2-6}$ alkenyl) group" means the above $C_{2-6}$ alkenyl group substituted by the above $C_{2-7}$ alkoxycarbonyl group.

The term "$C_{3-7}$ cycloalkyl group" or "$C_{3-7}$ cycloalkyl-" means a cyclopropyl group, a cyclobutyl group, a cyclopentyl group, a cyclohexyl group or a cycloheptyl group; the term "$C_{3-7}$ cycloalkyloxy group" means a hydroxy group substituted by the above $C_{3-7}$ cycloalkyl group; the term "$C_{3-7}$cycloalkyl($C_{1-6}$ alkyl) group" means the above $C_{1-6}$ alkyl group substituted by the above $C_{3-7}$ cycloalkyl group; the term "$C_{3-7}$ cycloalkyl($C_{1-6}$ alkoxy) group" means the above $C_{1-6}$ alkoxy group substituted by the above $C_{3-7}$ cycloalkyl group; and the term "$C_{3-7}$ cycloalkyl($C_{1-6}$ alkylthio) group" means the above $C_{1-6}$ alkylthio group substituted by the above $C_{3-7}$ cycloalkyl group. The term "heterocycloalkyl group" or "heterocycloalkyl-" means a 3 to 7-membered aliphatic heterocyclic group containing any 1 or 2 hetero atoms other than the binding position selected from an oxygen atom, a sulfur atom and a nitrogen atom in the ring, which is derived from morpholine, thiomorpholine, tetrahydrofuran, tetrahydropyran, aziridine, azetidine, pyrrolidine, imidazolidine, oxazoline, piperidine, piperazine, pyrazolidine, pyrroline, imidazoline or the like, or a 5 or 6-membered aliphatic heterocyclic group fused with a 6-membered ring containing any 1 or 2 hetero atoms other than the binding position selected from an oxygen atom, a sulfur atom and a nitrogen atom in the ring, which is derived from indoline, isoindoline, tetrahydroindoline, tetrahydroisoindoline, hexahydroindoline, hexahydroisoindoline or the like. The term "heterocycloalkyl($C_{1-6}$ alkyl) group" means the above $C_{1-6}$ alkyl group substituted by the above heterocycloalkyl group; the term "heterocycloalkyl($C_{1-6}$alkoxy) group" means the above $C_{1-6}$alkoxy group substituted by the above heterocycloalkyl group; and the term "heterocycloalkyl($C_{1-6}$ alkylthio) group" means the above $C_{1-6}$ alkylthio group substituted by the above heterocycloalkyl group.

The term "$C_{6-10}$ aryl group" or "$C_{6-10}$ aryl-" means an aromatic cyclic hydrocarbon group having 6 or 10 carbon atoms such as a phenyl group, a naphthyl group or the like; the term "$C_{6-10}$ aryl($C_{1-6}$ alkyl) group" means the above $C_{1-6}$ alkyl group substituted by the above $C_{6-10}$ aryl group; the term "$C_{6-10}$ aryl($C_{1-6}$ alkoxy) group" means the above $C_{1-6}$ alkoxy group substituted by the above $C_{6-10}$ aryl group; and the term "$C_{6-10}$ aryl($C_{1-6}$ alkylthio) group" means the above $C_{1-6}$ alkylthio group substituted by the above $C_{6-10}$ aryl group. The term "$C_{6-10}$ arylsulfonylamino group" means a sulfonylamino group having the above $C_{6-10}$ aryl group, such as a benzenesulfonylamino group or the like; the term "$C_{6-10}$ aryl ($C_{2-7}$ alkoxycarbonyl) group" means the above $C_{2-7}$ alkoxycarbonyl group substituted by the above $C_{6-10}$ aryl group; and the term "heteroaryl group" or "heteroaryl-" means a 5 or 6-membered aromatic heterocyclic group containing any 1 to 4 hetero atoms other than the binding position selected from an oxygen atom, a sulfur atom and a nitrogen atom in the ring, which is derived from thiazole, oxazole, isothiazole, isooxazole, pyridine, pyrimidine, pyrazine, pyridazine, pyrrole, thiophene, imidazole, pyrazole, oxadiazole, thiodiazole, tetrazole, furazan or the like, or a 5 or 6-membered aromatic heterocyclic group fused with a 6-membered aromatic ring containing any 1 to 4 hetero atoms other than the binding position selected from an oxygen atom, a sulfur atom and a nitrogen atom in the ring, which is derived from indole, isoindole, benzofuran, isobenzofuran, benzothiophen, benzooxazole, benzothiazole, indazole, benzoimidazole, quinoline, isoquinoline, phthalazine, quinoxaline, quinazoline, cinnoline, indolizine, naphthyridine, pteridine or the like. The term "heteroaryl($C_{1-6}$ alkyl) group" means the above $C_{1-6}$ alkyl group substituted by the above heteroaryl group; the term "heteroaryl($C_{1-6}$ alkoxy) group" means the above $C_{1-6}$ alkoxy group substituted by the above heteroaryl group; and the term "heteroaryl($C_{1-6}$ alkylthio) group" means the above $C_{1-6}$ alkylthio group substituted by the above heteroaryl group.

The term "aliphatic cyclic amino group" means a 5 or 6-membered aliphatic cyclic amino group which may contain one hetero atom other than the nitrogen atom at the binding position selected from an oxygen atom, a sulfur atom and nitrogen atom in the ring, such as a morpholino group, a thiomorpholino group, a 1-aziridinyl group, a 1-azetidinyl group, a 1-pyrrolidinyl group, a piperidino group, a 1-imidazolidinyl group, a 1-piperazinyl group, a pyrazolidinyl group or the like; the term "aromatic cyclic amino group" means a 5-membered aromatic cyclic amino group which may contain 1 to 3 nitrogen atoms in the ring other than the nitrogen atom at the binding position, such as a 1-imidazolyl group, a 1-pyrrolyl group, a pyrazolyl group, a 1-tetrazolyl group or the like; the term "aromatic cyclic amino($C_{1-6}$ alkyl) group" means the above $C_{1-6}$ alkyl group substituted by the above aromatic cyclic amino group; the term "aromatic cyclic amino($C_{1-6}$ alkoxy) group" means the above $C_{1-6}$ alkoxy group substituted by the above aromatic cyclic amino group; and the term "aromatic cyclic amino($C_{1-6}$ alkylthio) group" means the above $C_{1-6}$ alkylthio group substituted by the above aromatic cyclic amino group.

The term "hydroxy-protective group" means a hydroxy-protective group used in general organic synthesis such as a methyl group, a benzyl group, a methoxymethyl group, an acetyl group, a pivaloyl group, a benzoyl group, a tert-butyldimethylsilyl group, a tert-butyldiphenylsilyl group, an allyl group or the like; the term "amino-protective group" means an amino-protective group used in general organic synthesis such as a benzyloxycarbonyl group, a tert-butoxycarbonyl group, a benzyl group, an acetyl group, a trifluoroacetyl group or the like; and the term "carboxy-protective group" means a carboxy-protective group used in general organic synthesis such as a methyl group, an ethyl group, a benzyl group, a tert-butyldimethylsilyl group, an allyl group or the like. In addition, in the substituent Q, the left-hand bond means a bond bound to a nitrogen-containing fused ring and the right-hand bond means a bond bound to a ring A.

The compounds represented by the above general formula (I) of the present invention can be prepared according to the following procedures or analogous procedures thereof, or other procedures described in literatures or analogous procedures thereof.

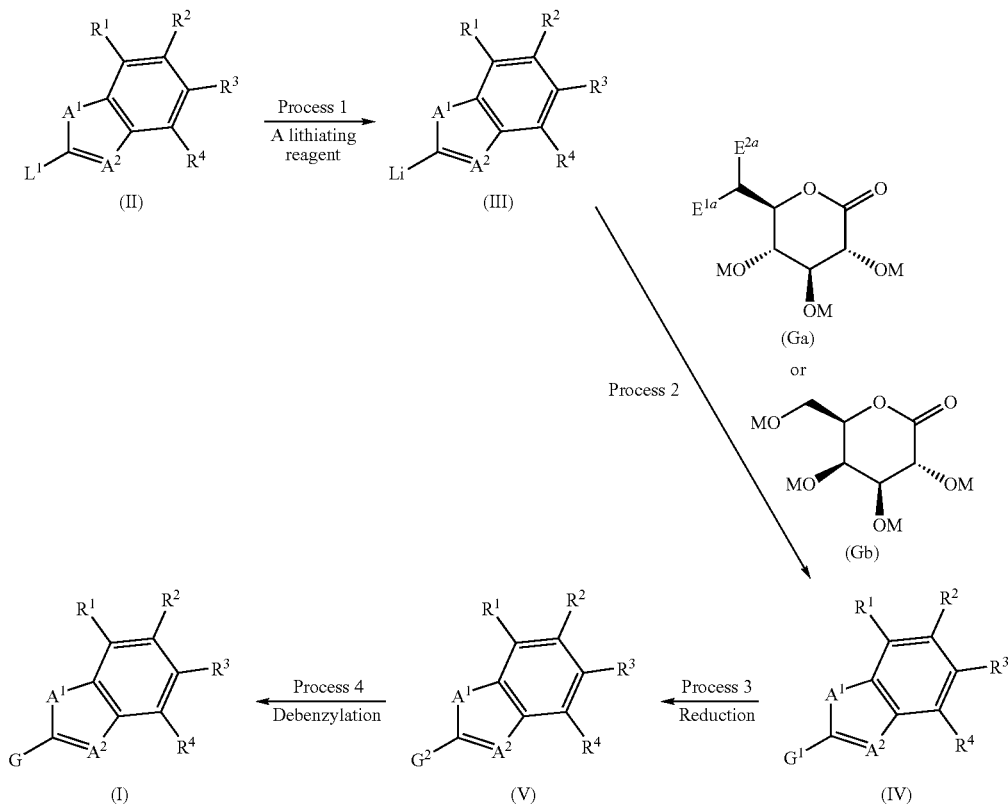

In the formula, $E^{1a}$ represents a hydrogen atom, a fluorine atome or a benzyloxy group; $E^{2a}$ represents a hydrogen atom, a fluorine atom, a methyl group or a benzyloxymethyl group; $L^1$ represents a hydrogen atom, a chlorine atom, a bromine atom or an iodine atom; M represents a benzyl group; $G^1$ represents a group represented by a formula:

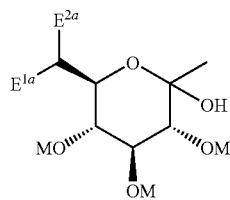

or a formula:

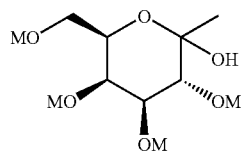

wherein M, $E^{1a}$ and $E^{2a}$ have the same meanings as defined above; $G^2$ represents the above G with a hydroxy group protected by a benzyl group; $R^1$ to $R^4$, $A^1$, $A^2$ and G have the same meanings as defined above and with the proviso that in the case that there are a hydroxy group, an amino group and/or a carboxy group in each compound, a compound having a protective group can be suitably used.

Process 1

A compound represented by the above general formula (III) can be prepared by subjecting a compound represented by the above general formula (II) to lithiation using a lithiating reagent such as n-butyllithium, sec-butyllithium, tert-butyllithium, lithium diisopropylamide or the like in an inert solvent. As the solvent used, for example, tetrahydrofuran, diethyl ether, a mixed solvent thereof and the like can be illustrated. The reaction temperature is usually from −100° C. to room temperature, and the reaction time is usually from 1 minute to 3 hours, varying based on a used starting material, solvent and reaction temperature.

Process 2

A compound represented by the above general formula (IV) can be prepared by subjecting a compound represented by the above general formula (III) to condensation with a sugar lactone represented by the above general formula (Ga) or (Gb) in an inert solvent. As the solvent used, for example, tetrahydrofuran, diethyl ether, a mixed solvent thereof and the like can be illustrated. The reaction temperature is usually from −100° C. to room temperature, and the reaction time is usually from 5 minutes to 5 hours, varying based on a used starting material, solvent and reaction temperature.

Process 3

A compound represented by the above general formula (V) can be prepared by subjecting a compound represented by the above general formula (IV) to reduction to remove a hydroxy group at the anomer-position using a reagent such as triethylsilane, triisopropylsilane or the like in the presence of boron trifluoride-diethyl ether complex in an inert solvent. As the solvent used, for example, acetonitrile, dichloromethane, 1,2-dichloroethane, a mixed solvent thereof and the like can be illustrated. The reaction temperature is usually from −20° C. to room temperature, and the reaction time is usually from 30 minutes to 1 day, varying based on a used starting material, solvent and reaction temperature.

Process 4

A compound represented by the above general formula (I) of the present invention can be prepared by subjecting a compound represented by the above general formula (V): 1) to catalytic hydrogenation using a palladium catalyst such as palladium-carbon powder or the like in an inert solvent or 2) to treatment using a reagent such as ethanethiol in the presence of an acid such as boron trifluoride-diethyl ether complex to remove the benzyl group in an inert solvent. As the solvent used in the catalytic hydrogenation, for example, methanol, ethanol, ethyl acetate, tetrahydrofuran, acetic acid, a mixed solvent thereof and the like can be illustrated. The reaction temperature is usually from 0° C. to reflux temperature, and the reaction time is usually from 1 hour to 2 days, varying based on a used starting material, solvent and reaction temperature. As the solvent used in the acid treatment, for example, dichloromethane, 1,2-dichloroethane, acetonitrile, a mixed solvent thereof and the like can be illustrated. The temperature is usually from 0° C. to reflux temperature, and the reaction time is usually from 30 minutes to 1 day, varying based on a used starting material, solvent and reaction temperature.

The starting materials used in the above manufacturing methods can be prepared according to procedures described in literatures or analogous procedures thereof. In addition, of the compounds represented by the above general formula (II), a compound represented by the following general formula (IIa), (IIb) or (IIc) can be also prepared according to the following Processes 5 to 9.

In the formula, one of L and L represents a hydrogen atom, a chlorine atom, a bromine atom or an iodine atom; and the other represents a hydrogen atom, a halogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy group, a $C_{2-7}$ alkoxycarbonyl($C_{1-6}$ alkyl) group, a carboxy($C_{1-6}$ alkyl) group, a $C_{3-7}$ cycloalkyl group or a $C_{3-7}$ cycloalkyl($C_{1-6}$ alkyl) group; $L^4$ represents —P(=O)($OR^0$)$_2$ or —P$^+$(PPh$_3$)$_3$X$^-$; $R^0$ represents a $C_{1-6}$ alkyl group; Ph represents a phenyl group; X represents a chlorine atom, a bromine atom or an iodine atom; one of $R^{10}$ and $R^{11}$ represents a group represented by a general formula:

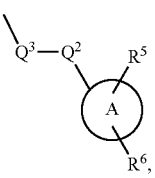

and the other represents a hydrogen atom, a halogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy group, a $C_{2-7}$ alkoxycarbonyl($C_{1-6}$ alkyl) group, a carboxy ($C_{1-6}$ alkyl) group, a $C_{3-7}$ cycloalkyl group or a $C_{3-7}$ cycloalkyl($C_{1-6}$ alkyl) group; one of $R^{12}$ and $R^{13}$ represents a group represented by a general formula:

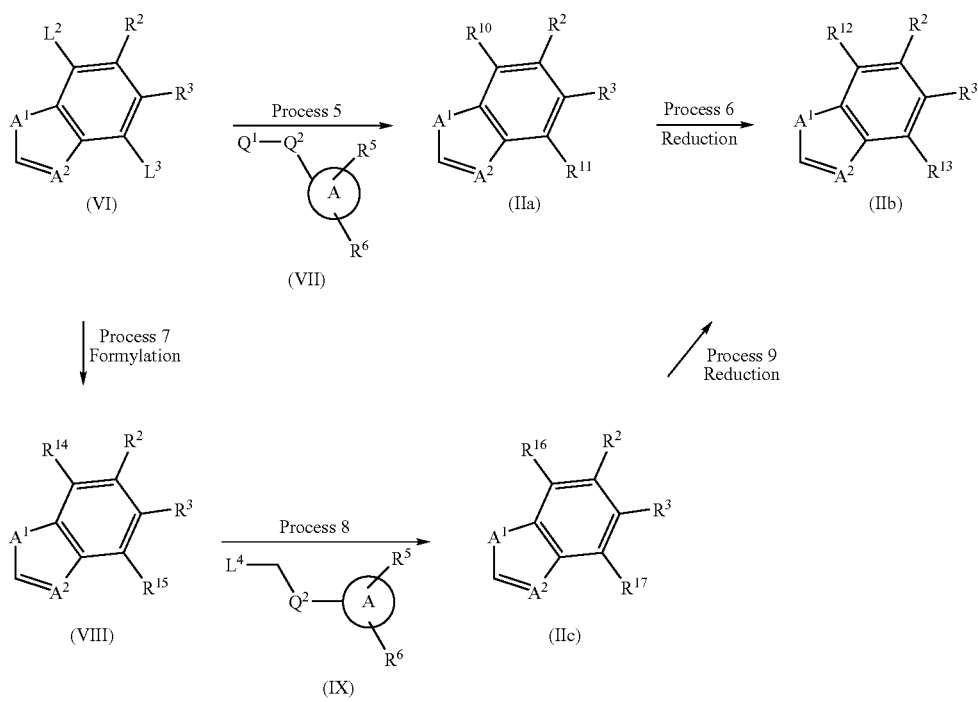

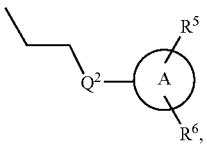

and the other represents a hydrogen atom, a halogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy group, a $C_{2-7}$ alkoxycarbonyl($C_{1-6}$ alkyl) group, a carboxy ($C_{1-6}$ alkyl) group, a $C_{3-7}$ cycloalkyl group or a $C_{3-7}$ cycloalkyl($C_{1-6}$ alkyl) group; one of $R^{14}$ and $R^{15}$ represents a formyl group and the other represents a hydrogen atom, a halogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy group, a $C_{2-7}$ alkoxycarbonyl($C_{1-6}$ alkyl) group, a carboxy($C_{1-6}$ alkyl) group, a $C_{3-7}$ cycloalkyl group or a $C_{3-7}$ cycloalkyl($C_{1-6}$ alkyl) group; one of $R^{16}$ and $R^{17}$ represents a group represented by a general formula:

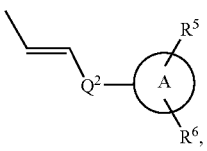

and the other represents a hydrogen atom, a halogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy group, a $C_{2-7}$ alkoxycarbonyl($C_{1-6}$ alkyl) group, a carboxy ($C_{1-6}$ alkyl) group, a $C_{3-7}$ cycloalkyl group or a $C_{3-7}$ cycloalkyl($C_{1-6}$ alkyl) group; $Q^1$ represents a vinyl group or an ethynyl group; $Q^2$ represents a single bond, —$C_{1-4}$ alkylene-, —$C_{2-4}$ alkenylene-, —$C_{2-4}$ alkynylene-, —$C_{1-4}$ alkylene-O—, —$C_{1-4}$ alkylene-S—, —$C_{1-4}$ alkylene-O—$C_{1-6}$ alkylene- or —$C_{1-4}$ alkylene-S—$C_{1-6}$ alkylene-; $Q^3$ represents a vinylene group or an ethynylene group; and $R^2$, $R^3$, $R^5$, $R^6$, $A^1$, $A^2$ and ring A have the same meanings as defined above.

Process 5

A compound represented by the above general formula (IIa) can be prepared by subjecting a compound represented by the above general formula (VI) to Heck reaction or Sonogashira reaction with a compound represented by the above general formula (VII) using a palladium catalyst such as palladium-carbon powder, palladium acetate, tetrakis(triphenylphosphine)palladium, dibenzylideneacetone palladium, bis(triphenylphosphine)palladium dichloride or the like in the presence or absence of a ligand such as tris(2-methylphenyl)phosphine, triphenylphosphine or the like in the presence of a base such as triethylamine, N,N-diisopropylethylamine, sodium tert-butoxide, potassium tert-butoxide, sodium carbonate, potassium carbonate, cesium fluoride or the like and in the presence or absence of copper (I) iodide in an inert solvent. As the solvent used, for example, acetonitrile, toluene, tetrahydrofuran, triethylamine, N,N-diisopropylethylamine, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 6

A compound represented by the above general formula (IIb) can be prepared by subjecting a compound represented by the above general formula (IIa): 1) to catalytic hydrogenation using a palladium catalyst such as palladium-carbon powder in an inert solvent, or 2) to diimide reduction in the presence or absence of a base such as triethylamine, N,N-diisopropylethylamine or the like using a reagent such as 2,4,6-triisopropylbenzenesulfonyl hydrazide or the like in an inert solvent. As the solvent used in the catalytic hydrogenation, for example, methanol, ethanol, ethyl acetate, tetrahydrofuran, acetic acid, a mixed solvent thereof and the like can be illustrated. The reaction temperature is usually from 0° C. to reflux temperature, and the reaction time is usually from 1 hour to 2 days, varying based on a used starting material, solvent and reaction temperature. As the solvent used in the diimide reduction, for example, tetrahydrofuran, diethyl ether, a mixed solvent thereof and the like can be illustrated. The reaction temperature is usually from room temperature to reflux temperature, and the reaction time is usually from 1 hour to 3 days, varying based on a used starting material, solvent and reaction temperature.

Process 7

A compound represented by the above general formula (VIII) can be prepared by subjecting a compound represented by the above general formula (VI) 1) to lithiation in the presence or absence of an additive such as N,N,N',N'-tetramethylethylenediamine, hexamethylphosphoramide or the like using a base such as n-butyllithium, sec-butyllithium, tert-butyllithium or the like in an inert solvent or preparation of a Grignard reagent in the presence of an additive such as iodine, 1,2-dibromoethane or the like using magnesium in an inert solvent, and then 2) to formylation using N,N-dimethylformamide. As the solvent used, for example, tetrahydrofuran, diethyl ether, a mixed solvent thereof and the like can be illustrated. The reaction temperature is usually from −100° C. to reflux temperature in the reaction 1) and usually from −100° C. to room temperature in the reaction 2), and the reaction time is usually from 1 minute to 1 hour in the reaction 1) and usually from 30 minutes to 1 day in the reaction 2), varying based on a used starting material, solvent and reaction temperature.

Process 8

A compound represented by the above general formula (IIc) can be prepared by subjecting a compound represented by the above general formula (VIII) to Wittig reaction or Horner-Emmons reaction in the presence of a base such as sodium hydride, sodium hydroxide, potassium tert-butoxide, n-butyllithium, tert-butyllithium or the like using a compound represented by the above general formula (IX) in an inert solvent. As the solvent used in the reaction, for example, tetrahydrofuran, N,N-dimethylformamide, dimethylsulfoxide, methanol, ethanol, acetonitrile, water, a mixed solvent thereof and the like can be illustrated. The temperature is usually from 0° C. to reflux temperature, and the reaction time is usually from 30 minutes to 1 day, varying based on a used starting material, solvent and reaction temperature.

Process 9

A compound represented by the above general formula (IIb) can be prepared by subjecting a compound represented by the above general formula (IIc) 1) to catalytic hydrogenation using a palladium catalyst such as palladium-carbon powder or the like in an inert solvent or 2) to diimide reduction in the presence or absence of a base such as triethylamine, N,N-diisopropylethylamine or the like using a reagent such as 2,4,6-triisopropylbenzenesulfonylhydrazide or the like in an inert solvent. As the solvent used in the catalytic hydrogenation, for example, methanol, ethanol, ethyl acetate, tetrahydrofuran, acetic acid, a mixed solvent thereof and the like can be illustrated. The temperature is usually from 0° C. to reflux temperature, and the reaction time is usually from 1 hour to 2 days, varying based on a used starting material, solvent and reaction temperature. As the solvent used in the diimide reduction, for example, tetrahydrofuran, diethyl ether, a mixed solvent thereof and the like can be illustrated. The temperature is usually from room temperature to reflux temperature, and the reaction time is usually from 1 hour to 3 days, varying based on a used starting material, solvent and reaction temperature.

Of the compounds represented by the above general formula (II), a compound wherein A is a sulfur atom; A is a carbon atom; and L is a hydrogen atom can be also prepared according to the following Processes 10 to 11 or 12 to 15.

In the formula, $L^5$ represents a chlorine atom, a bromine atom or an iodine atom; R represents a methyl group or an ethyl group, or both R are bound together to form an ethylene group or a trimethylene group; $R^{18}$ represents a methyl group or an ethyl group; and $R^1$ to $R^4$ have the same meanings as defined above.

Process 10

A compound represented by the above general formula (XII) can be prepared by subjecting a compound represented by the above general formula (X) to S-alkylation in the presence of a base such as potassium carbonate, cesium carbonate, triethylamine, N,N-diisopropylethylamine or the like using a compound represented by the above general formula (XI) in an inert solvent. As the solvent used, for example, N,N-dimethylformamide, acetone, dichloromethane, a mixed solvent thereof and the like can be illustrated. The reaction temperature is usually from 0° C. to reflux tempera-

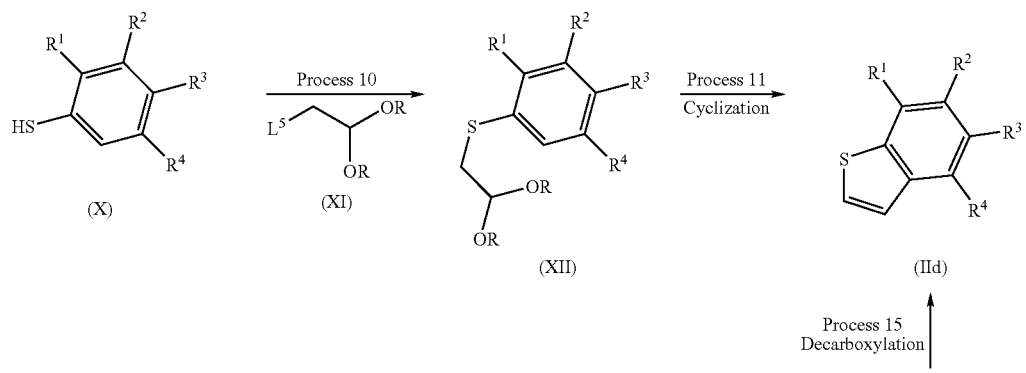

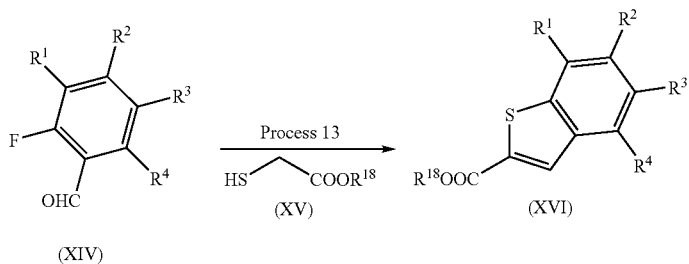

ture, and the reaction time is usually from 30 minutes to 1 day, varying based on a used starting material, solvent and reaction temperature.

Process 11

A benzothiophene derivative represented by the above general formula (IId) can be prepared by subjecting a compound represented by the above general formula (XII) to cyclization in the presence of polyphosphoric acid in an inert solvent. As the solvent used, for example, benzene, chlorobenzene, toluene and the like can be illustrated. The temperature is usually from room temperature to reflux temperature, and the reaction time is usually from 1 hour to 1 day, varying based on a used starting material, solvent and reaction temperature.

Process 12

A compound represented by the above general formula (XIV) can be prepared by subjecting a compound represented by the above general formula (XIII) 1) to lithiation in the presence or absence of an additive such as N,N,N',N'-tetramethylethylenediamine, hexamethylphosphoramide or the like using a base such as n-butyllithium, sec-butyllithium, tert-butyllithium, lithium diisopropylaminde or the like in an inert solvent and then 2) to formylation using N,N-dimethylformamide. As the solvent used, for example, tetrahydrofuran, diethyl ether, a mixed solvent thereof and the like can be illustrated. The reaction temperature is usually from −100° C. to 0° C. in the reaction 1) and usually from −100° C. to room temperature in the reaction 2), and the reaction time is usually from 30 minutes to 5 hours in the reaction 1) and usually from 30 minutes to 1 day in the reaction 2), varying based on a used starting material, solvent and reaction temperature.

Process 13

A benzothiophene derivative represented by the above general formula (XVI) can be prepared by subjecting a compound represented by the above general formula (XIV) to cyclization in the presence of a base such as triethylamine, N,N-diisopropylethylamine, potassium carbonate, cesium carbonate, potassium tert-butoxide, sodium hydride or the like using a mercaptoacetic acid ester represented by the above general formula (XV) in an inert solvent. As the solvent used, for example, N,N-dimethylformamide, dimethylsulfoxide, tetrahydrofuran, methanol, ethanol, n-butanol and the like can be illustrated. The reaction temperature is usually from room temperature to reflux temperature, and the reaction time is usually from 1 hour to 1 day, varying based on a used starting material, solvent and reaction temperature.

Process 14

A carboxylic acid derivative represented by the above general formula (XVII) can be prepared by subjecting a compound represented by the above general formula (XVI) to hydrolysis in the presence of a basic substance such as sodium hydroxide, potassium hydroxide or the like. As the solvent used, for example, methanol, ethanol, 2-propanol, tetrahydrofuran, water, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 15

A compound represented by the above general formula (IId) can be prepared by subjecting a compound represented by the above general formula (XVII) to decarboxylation using a catalyst such as cupper powder or the like in an inert solvent. As the solvent used, for example, quinoline and the like can be illustrated. The reaction temperature is usually from 100° C. to reflux temperature, and the reaction time is usually from 30 minutes to 1 day, varying based on a used starting material, solvent and reaction temperature.

Of the compounds represented by the above general formula (II), a compound wherein $L^1$ is a hydrogen atom; one of $R^1$ and $R^4$ is a chlorine atom, a bromine atom or an iodine atom and the other is a hydrogen atom, a halogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy group, a $C_{2-7}$ alkoxycarbonyl($C_{1-6}$ alkyl) group, a carboxy($C_{1-6}$ alkyl) group, a $C_{3-7}$ cycloalkyl group or a $C_{3-7}$ cycloalkyl($C_{1-6}$ alkyl) group; and $R^9$ is a $C_{1-6}$ alkyl group; can be also prepared according to the following Processes 16 to 18.

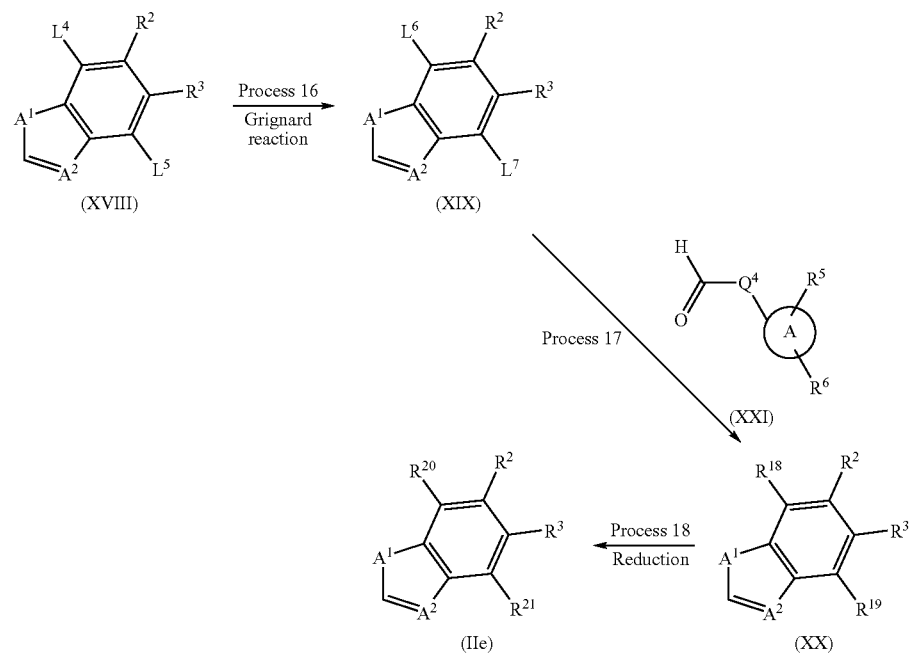

In the formula, one of L and L represents a chlorine atom, a bromine atom or an iodine atom and the other represents a hydrogen atom, a halogen atom, a $C_{1-6}$ alkyl group, a halo($C_{1-6}$ alkyl) group, a hydroxy($C_{1-6}$ alkyl) group, a dihydroxy ($C_{1-6}$ alkyl) group, a $C_{1-6}$ alkoxy group, a $C_{2-7}$ alkoxycarbonyl ($C_{1-6}$ alkyl) group, a carboxy($C_{1-6}$ alkyl) group, a $C_{3-7}$ cycloalkyl group or a $C_{3-7}$ cycloalkyl($C_{1-6}$ alkyl) group; one of $L^6$ and $L^7$ represents MgCl, MgBr or MgI and the other represents a hydrogen atom, a halogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy group, a $C_{2-7}$ alkoxycarbonyl($C_{1-6}$ alkyl) group, a carboxy($C_{1-6}$ alkyl) group, a $C_{3-7}$ cycloalkyl group or a $C_{3-7}$ cycloalkyl($C_{1-6}$ alkyl) group; Q represents a single bond, —$C_{1-5}$ alkylene-, —$C_{2-5}$- alkenylene-, —$C_{2-5}$ alkynylene-, —$C_{1-5}$ alkylene-O—, —$C_{1-5}$ alkylene-S—, —$C_{1-5}$ alkylene-O—$C_{1-6}$ alkylene-, —$C_{1-5}$ alkylene-S—$C_{1-6}$ alkylene- or —$C_{1-5}$ alkylene-CON ($R^6$)—; one of $R^{18}$ and $R^{19}$ represents a group represented by a general formula:

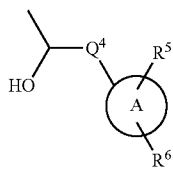

and the other represents a hydrogen atom, a halogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy group, a $C_{2-7}$ alkoxycarbonyl($C_{1-6}$ alkyl) group, a carboxy ($C_{1-6}$ alkyl) group, a $C_{3-7}$ cycloalkyl group or a $C_{3-7}$ cycloalkyl($C_{1-6}$ alkyl) group; one of $R^{20}$ and $R^{21}$ represents a group represented by a general formula:

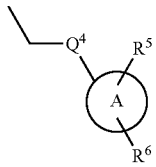

and the other represents a hydrogen atom, a halogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy group, a $C_{2-7}$ alkoxycarbonyl($C_{1-6}$ alkyl) group, a carboxy ($C_{1-6}$ alkyl) group, a $C_{3-7}$ cycloalkyl group or a $C_{3-7}$ cycloalkyl($C_{1-6}$ alkyl) group; and ring A, $A^1$, $A^2$, $R^2$, $R^3$, $R^5$, $R^6$ and $R^8$ have the same meanings as defined above.

Process 16

A Grignard reagent represented by the above general formula (XIX) can be prepared by allowing a compound represented by the above general formula (XVIII) to react with magnesium metal in the presence of an activating agent such as a catalytic amount of iodine or the like in an inert solvent. As the solvent used, for example, diethyl ether, tetrahydrofuran, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 17

An alcohol derivative represented by the above general formula (XX) can be prepared by allowing a compound represented by the above general formula (XXI) to react with a Grignard reagent represented by the above general formula (XIX) in an inert solvent. As the solvent used, for example, diethyl ether, tetrahydrofuran and the like can be illustrated. The reaction temperature is usually from −20° C. to reflux temperature, and the reaction time is usually from 30 minutes to 1 day, varying based on a used starting material, solvent and reaction temperature.

Process 18

A benzothiophen derivative represented by the above general formula (IIe) can be prepared by subjecting an alcohol derivative represented by the above general formula (XX) to reduction in the presence of iodotrimethylsilane in an inert solvent. As the solvent used, for example, acetonitrile and the like can be illustrated. The reaction temperature is usually from −20° C. to reflux temperature, and the reaction time is usually from 15 minutes to 1 day, varying based on a used starting material, solvent and reaction temperature.

Of the compounds represented by the above general formula (II), a compound represented by the following general formula (IIf) can be also prepared according to the following Process 19.

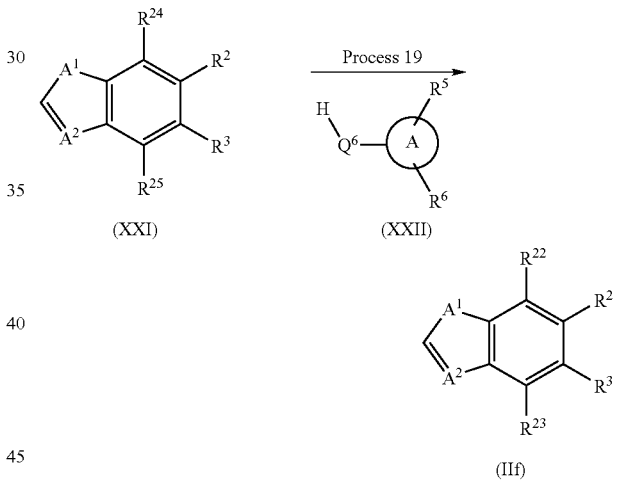

In the formula, one of $R^{22}$ and $R^{23}$ represents a group represented by a general formula:

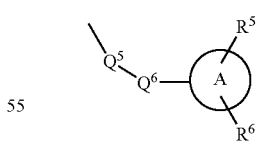

wherein $Q^5$ represents —$C_{1-6}$ alkylene-; $Q^6$ represents an oxygen atom, a sulfur atom, —O—$C_{1-6}$ alkyl- or —S—$C_{1-6}$ alkyl-; $R^5$, $R^6$ and ring A have the same meanings as defined above, and the other represents a hydrogen atom, a hydroxy group, an amino group, a halogen atom, a $C_{1-6}$ alkyl group, a $C_{1-6}$ alkoxy group, a cyano group, a carboxy group, a $C_{2-7}$ alkoxycarbonyl group, a carbamoyl group, a mono or di($C_{1-6}$ alkyl)amino group, a halo($C_{1-6}$ alkyl) group, a hydroxy($C_{1-6}$ alkyl) group, a cyano($C_{1-6}$ alkyl) group, a carboxy($C_{1-6}$ alkyl)

group, a $C_{2-7}$ alkoxycarbonyl($C_{1-6}$ alkyl) group, a carbamoyl ($C_{1-6}$ alkyl) group, an amino($C_{1-6}$ alkyl) group, a mono or di($C_{1-6}$ alkyl)amino($C_{1-6}$ alkyl) group, a halo($C_{1-6}$ alkoxy) group, a hydroxy($C_{1-6}$ alkoxy) group, a carboxy($C_{1-6}$ alkoxy) group, a $C_{2-7}$ alkoxycarbonyl($C_{1-6}$ alkoxy) group, a carbamoyl($C_{1-6}$ alkoxy) group, an amino($C_{1-6}$ alkoxy) group, a mono or di($C_{1-6}$ alkyl)amino($C_{1-6}$ alkoxy) group, a $C_{3-7}$ cycloalkyl group, a $C_{3-7}$ cycloalkyloxy group, a $C_{3-7}$ cycloalkyl($C_{1-6}$ alkyl) group or a $C_{3-7}$ cycloalkyl($C_{1-6}$ alkoxy) group; one of $R^{24}$ and $R^{25}$ represents a group represented by a general formula:

-$Q^5$-$L^8$ wherein $L^8$ represents a chlorine atom, a bromine atom, an iodine atom, a mesyloxy group or a tosyloxy group; $Q^5$ has the same meaning as defined above, and the other represents a hydrogen atom, a hydroxy group, an amino group, a halogen atom, a $C_{1-6}$ alkyl group, a $C_{1-6}$ alkoxy group, a cyano group, a carboxy group, a $C_{2-7}$ alkoxycarbonyl group, a carbamoyl group, a mono or di($C_{1-6}$ alkyl)amino group, a halo($C_{1-6}$ alkyl) group, a hydroxy($C_{1-6}$ alkyl) group, a cyano($C_{1-6}$ alkyl) group, a carboxy($C_{1-6}$ alkyl) group, a $C_{2-7}$ alkoxycarbonyl ($C_{1-6}$ alkyl) group, a carbamoyl($C_{1-6}$ alkyl) group, an amino ($C_{1-6}$ alkyl) group, a mono or di($C_{1-6}$ alkyl)amino($C_{1-6}$ alkyl) group, a halo($C_{1-6}$ alkoxy) group, a hydroxy($C_{1-6}$ alkoxy) group, a carboxy($C_{1-6}$ alkoxy) group, a $C_{2-7}$ alkoxycarbonyl ($C_{1-6}$ alkoxy) group, a carbamoyl($C_{1-6}$ alkoxy) group, an amino($C_{1-6}$ alkoxy) group, a mono or di($C_{1-6}$ alkyl)amino ($C_{1-6}$ alkoxy) group, a $C_{3-7}$ cycloalkyl group, a $C_{3-7}$ cycloalkyloxy group, a $C_{3-7}$ cycloalkyl($C_{1-6}$ alkyl) group or a $C_{3-7}$ cycloalkyl($C_{1-6}$ alkoxy) group; and $A^1$, $A^2$, $R^2$ and $R^3$ have the same meanings as defined above.

Process 19

A compound represented by the above general formula (IIf) can be prepared by subjecting a compound represented by the above general formula (XXI) to condensation with a compound represented by the above general formula (XXII) in the presence of a base such as sodium hydride, potassium hydroxide, potassium tert-butoxide, cesium carbonate or the like in an inert solvent. As the solvent used in the condensation reaction, for example, tetrahydrofuran, N,N-dimethylformamide, dimethylsulfoxide, acetone, methanol, a mixed solvent thereof and the like can be illustrated. The reaction temperature is usually from 0° C. to reflux temperature, and the reaction time is usually from 1 hour to 1 day, varying based on a used starting material, solvent and reaction temperature.

In case of compounds having a hydroxy group, an amino group and/or a carboxy group in the above procedures, they can be also used in each reaction after introducing any protective group in the usual way as occasion demand. The protective group can be optionally removed in any subsequent reaction in the usual way.

The compounds represented by the above general formula (I) of the present invention obtained by the above production processes can be isolated and purified by conventional separation means such as fractional recrystallization, purification using chromatography, solvent extraction and solid phase extraction.

The fused heterocyclic derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lacetic acid, malic acid, carbonic acid, glutamic acid, aspartic acid and the like, salts with inorganic bases such as a sodium salt, a potassium salt and the like, and salts with organic bases such as N-methyl-D-glucamine, N,N'-dibenzyletylenediamine, 2-aminoethanol, tris(hydroxymethyl)aminomethane, arginine, lysine and the like.

The compounds represented by the above general formula (I) of the present invention include their solvates with pharmaceutically acceptable solvents such as water and ethanol.

Of the fused heterocyclic derivatives represented by the above general formula (I) of the present invention and the prodrugs thereof, there are two geometrical isomers, cis(Z)-isomer and trans(E)-isomer, in each compound having an unsaturated bond. In the present invention, either of the isomers can be employed.

Of the fused heterocyclic derivatives represented by the above general formula (I) of the present invention and the prodrugs thereof, there are two optical isomers, R-isomer and S-isomer, in each compound having an asymmetric carbon atom excluding the sugar moiety. In the present invention, either of the optical isomers can be employed, and a mixture of both optical isomers can be also employed.

A prodrug of a compound represented by the above general formula (I) of the present invention can be prepared by introducing an appropriate group forming a prodrug into any one or more groups selected from a hydroxy group, an amino group and a cyclic amino group such as a pyrazole ring, a piperazine ring or the like of the compound represented by the above general formula (I) using a corresponding reagent to produce a prodrug such as a halide compound or the like in the usual way, and then by suitably isolating and purificating in the usual way as occasion demands. As a group forming a prodrug used in a hydroxy group or an amino group, for example, a $C_{2-7}$ acyl group, a $C_{1-6}$ alkoxy($C_{2-7}$ acyl) group, a $C_{2-7}$ alkoxycarbonyl($C_{2-7}$ acyl) group, a $C_{2-7}$ alkoxycarbonyl group, a $C_{6-10}$ aryl($C_{2-7}$ alkoxycarbonyl) group, a $C_{1-6}$ alkoxy ($C_{2-7}$ alkoxycarbonyl) group or the like can be illustrated. As a group forming a prodrug used in a cyclic amino group, for example, a $C_{2-7}$ acyl group, a $C_{1-6}$ alkoxy($C_{2-7}$ acyl) group, a $C_{2-7}$ alkoxycarbonyl($C_{2-7}$ acyl) group, a $C_{2-7}$ alkoxycarbonyl group, a $C_{6-10}$ aryl($C_{2-7}$ alkoxycarbonyl) group, a $C_{1-6}$ alkoxy ($C_{2-7}$ alkoxycarbonyl) group, a ($C_{2-7}$ acyloxy)methyl group, a 1-($C_{2-7}$ acyloxy)ethyl group, a ($C_{2-7}$ alkoxycarbonyl)oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)oxycarbonyloxy]ethyl group or the like can be illustrated. The term "$C_{1-6}$ alkoxy($C_{2-7}$ acyl) group" means the above $C_{2-7}$ acyl group substituted by the above $C_{1-6}$ alkoxy group; the term "$C_{2-7}$ alkoxycarbonyl($C_{2-7}$ acyl) group" means the above $C_{2-7}$ acyl group substituted by the above $C_{2-7}$ alkoxycarbonyl group; the term "$C_{1-6}$ alkoxy($C_{2-7}$ alkoxycarbonyl) group" means the above $C_{2-7}$ alkoxycarbonyl group substituted by the above $C_{1-6}$ alkoxy group. The term "($C_{2-7}$ acyloxy)methyl group" means a hydroxymethyl group O-substituted by the above $C_{2-7}$ acyl group; the term "1-($C_{2-7}$ acyloxy)ethyl group" means a 1-hydroxyethyl group O-substituted by the above $C_{2-7}$ acyl group; the term "($C_{2-7}$ alkoxycarbonyl)oxymethyl group" means a hydroxymethyl group O-substituted by the above $C_{2-7}$ alkoxycarbonyl group; the term "1-[($C_{2-7}$ alkoxycarbonyl)oxy]ethyl group" means a 1-hydroxyethyl group O-substituted by the above $C_{2-7}$ alkoxycarbonyl group; the term "($C_{3-7}$ cycloalkyl)oxycarbonyl group" means a cyclic alkoxycarbonyl group having the above $C_{3-7}$ cycloalkyl group; the term "($C_{3-7}$ cycloalkyl)oxycarbonyloxymethyl group" means a hydroxymethyl group O-substituted by the above ($C_{3-7}$ cycloalkyl)oxycarbonyl group; and the term "1-[($C_{3-7}$ cycloalkyl)oxycarbonyloxy]ethyl group" means a 1-hydroxyethyl group O-substituted by the above ($C_{3-7}$ cycloalkyl)oxycarbonyl group. In addition, as a group forming a prodrug, a glucopyranosyl group or a galactopyranosyl group can be illustrated. For example, these groups are preferably introduced into the hydroxy group at the 4 or 6 position of the glucopyranosyloxy group or the galactopyranosyloxy group, and are more preferably introduced into the hydroxy group at the 4 or 6 position of the glucopyranosyloxy group.

The fused heterocyclic derivatives represented by the above general formula (I) of the present invention, for example, showed a potent inhibitory activity on human SGLT1 or SGLT2 in a human SGLT1 or SGLT2 inhibitory activity confirmatory test as described below. Therefore, a fused heterocyclic derivative represented by the above general formula (I) of the present invention can exert an excellent inhibitory activity of SGLT1 at the small intestine or an excellent inhibitory activity of SGLT2 at the kidney, and significantly inhibit blood glucose level increase or significantly lower blood glucose level. Therefore, a fused heterocyclic derivative represented by the above general formula (I) of the present invention, a pharmaceutically acceptable salt thereof and a prodrug thereof is extremely useful as an agent for the inhibition of postprandial hyperglycemia, the inhibition of advancing into diabetes in a subject with impaired glucose tolerance and the prevention or treatment of a disease associated with hyperglycemia such as diabetes, impaired glucose tolerance (IGT), diabetic complications (e.g., retinopathy, neuropathy, nephropathy, ulcer, macroangiopathy), obesity, hyperinsulinemia, hyperlipidemia, hypercholesterolemia, hypertriglyceridemia, lipid metabolism disorder, atherosclerosis, hypertension, congestive heart failure, edema, hyperuricemia, gout or the like, which relates to SGLT1 activity at the small intestine and SGLT2 activity at the kidney.

Furthermore, the compounds of the present invention can be suitably used in combination with at least one member selected from the following drugs. Examples of the drugs which can be used in combination with the compounds of the present invention include an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhydantoin, EGB-761, bimoclomol, sulodexide, Y-128, an antidiarrhoics, cathartics, a hydroxymethylglutaryl coenzyme A reductase inhibitor, a fibrate, a $β_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of the same or different administration route, and administration at different dosage intervals as separated preparations in way of the same or different administration route. A pharmaceutical combination comprising the compound of the present invention and the above drug(s) includes both dosage forms as a single preparation and separated preparations for combination as mentioned above.

The compounds of the present invention can obtain more advantageous effects than additive effects in the prevention or treatment of the above diseases when using suitably in combination with the above one or more drugs. Also, the administration dose can be decreased in comparison with administration of either drug alone, or adverse effects of coadministered drugs can be avoided or declined.

Concrete compounds as the drugs used for combination and preferable diseases to be treated are exemplified as follows. However, the present invention is not limited thereto, and the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for diabetes, impaired glucose tolerance or hyperinsulinemia because of improving the disturbance of insulin signal transduction in peripheral tissues and enhancing glucose uptake into the tissues from the blood, leading to lowering of blood glucose level.

As glucose absorption inhibitors, for example, α-glucosidase inhibitors such as acarbose, voglibose, miglitol, CKD-711, emiglitate, MDL-25,637, camiglibose and MDL-73,945, α-amylase inhibitors such as AZM-127, SGLT1 inhibitors described in pamphlets of International Publication Nos. WO02/098893, WO2004/014932 and the like are illustrated. Glucose absorption inhibitors are used preferably for diabetes, impaired glucose tolerance, diabetic complications, obesity or hyperinsulinemia, and more preferably for impaired glucose tolerance because of inhibiting the gastrointestinal enzymatic digestion of carbohydrates contained in foods, and inhibiting or delaying the absorption of glucose into the body.

As biguanides, phentormin, butormin hydrochloride, metformin hydrochloride or the like are illustrated. Biguanides are used preferably for diabetes, impaired glucose tolerance, diabetic complications or hyperinsulinemia, and more preferably for diabetes, impaired glucose tolerance or hyperinsulinemia because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxepide, glybuthiazol, glybuzole, glyhexamide, sodium glymidine, glypinamide, phenbutamide, tolcyclamide, glimepiride, nateglinide, mitiglinide calcium hydrate, repaglinide or the like are illustrated. In addition, the insulin secretion enhancers include glucokinase activators such as RO-28-1675. Insulin secretion enhancers are used preferably for diabetes, impaired glucose tolerance or diabetic complications, and more preferably for diabetes or impaired glucose tolerance because of lowering blood glucose level by acting on pancreatic β-cells and enhancing the insulin secretion.

As SGLT2 inhibitors, T-1095 and compounds described in Japanese patent publications Nos. Hei10-237089 and 2001-288178, and International Publications Nos. WO01/16147, WO01/27128, WO01/68660, WO01/74834, WO01/74835, WO02/28872, WO02/36602, WO02/44192, WO02/53573, WO03/000712, WO03/020737 and the like are illustrated. SGLT2 inhibitors are used preferably for diabetes, impaired glucose tolerance, diabetic complications, obesity or hyperinsulinemia, and more preferably for diabetes, impaired glucose tolerance, obesity or hyperinsulinemia because of lowering blood glucose level by inhibiting the reabsorption of glucose at the kidney's proximal tubule.

As insulin or insulin analogues, human insulin, animal-derived insulin, human or animal-derived insulin analogues or the like are illustrated. These preparations are used preferably for diabetes, impaired glucose tolerance or diabetic complications, and more preferably for diabetes or impaired glucose tolerance.

As glucagon receptor antagonists, BAY-27-9955, NNC-92-1687 or the like are illustrated; as insulin receptor kinase stimulants, TER-17411, L-783281, KRX-613 or the like are illustrated; as tripeptidyl peptidase II inhibitors, UCL-1397 or the like are illustrated; as dipeptidyl peptidase IV inhibitors, NVP-DPP728A, TSL-225, P-32/98 or the like are illustrated; as protein tyrosine phosphatase 1B inhibitors, PTP-112, OC-86839, PNU-177496 or the like are illustrated; as glycogen phosphorylase inhibitors, NN-4201, CP-368296 or the like are illustrated; as fructose-bisphosphatase inhibitors, R-132917 or the like are illustrated; as pyruvate dehydrogenase inhibitors, AZD-7545 or the like are illustrated; as hepatic gluconeogenesis inhibitors, FR-225659 or the like are illustrated; as glucagon-like peptide-1 analogues, exendin-4, CJC-1131 or the like are illustrated; as glucagon-like peptide 1 agonists; AZM-134, LY-315902 or the like are illustrated; and as amylin, amylin analogues or amylin agonists, pramlintide acetate or the like are illustrated. These drugs, glucose-6-phosphatase inhibitors, D-chiroinsitol, glycogen synthase kinase-3 inhibitors and glucagon-like peptide-1 are used preferably for diabetes, impaired glucose tolerance, diabetic complications or hyperinsulinemia, and more preferably for diabetes or impaired glucose tolerance.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat or the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation end products formation inhibitors, pyridoxamine, OPB-9195, ALT-946, ALT-711, pimagedine hydrochloride or the like are illustrated. Advanced glycation endproducts formation inhibitors are preferably used for diabetic complications because of inhibiting formation of advanced glycation endproducts which are accelerated in continuous hyperglycemic condition in diabetes and declining of cellular damage.

As protein kinase C inhibitors, LY-333531, midostaurin or the like are illustrated. Protein kinase C inhibitors are preferably used for diabetic complications because of inhibiting of protein kinase C activity which is accelerated in continuous hyperglycemic condition in diabetes.

As γ-aminobutyric acid receptor antagonists, topiramate or the like are illustrated; as sodium channel antagonists, mexiletine hydrochloride, oxcarbazepine or the like are illustrated; as transcript factor NF-κB inhibitors, dexlipotam or the like are illustrated; as lipid peroxidase inhibitors, tirilazad mesylate or the like are illustrated; as N-acetylated-α-linked-acid-dipeptidase inhibitors, GPI-5693 or the like are illustrated; and as carnitine derivatives, carnitine, levacecamine hydrochloride, levocarnitine chloride, levocarnitine, ST-261 or the like are illustrated. These drugs, insulin-like growth factor-I, platelet-derived growth factor, platelet derived growth factor analogues, epidermal growth factor, nerve growth factor, uridine, 5-hydroxy-1-methylhydantoin, EGB-761, bimoclomol, sulodexide and Y-128 are preferably used for diabetic complications.

As antidiarrhoics or cathartics, polycarbophil calcium, albumin tannate, bismuth subnitrate or the like are illustrated. These drugs are preferably used for diarrhea, constipation or the like accompanying diabetes or the like.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin or the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibrates, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 or the like are illustrated. Fibrates are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering of blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178 or the like are illustrated. $\beta_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $\beta_3$-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe or the like are illustrated. Acyl-coenzyme A cholesterol acyltransferase inhibitors are used preferably for hyperlipidemia, hyper-cholesterolemia, hypertriglyceridemia or lipid metabolism disorder, and more preferably for hyperlipidemia or hyper-cholesterolemia because of lowering blood cholesterol level by inhibiting acyl-coenzyme A cholesterol acyltransferase.

As thyroid hormone receptor agonists, sodium liothyronine, sodium levothyroxine, KB-2611 or the like are illustrated; as cholesterol absorption inhibitors, ezetimibe, SCH-48461 or the like are illustrated; as lipase inhibitors, orlistat, ATL-962, AZM-131, RED-103004 or the like are illustrated; as carnitine palmitoyltransferase inhibitors, etomoxir or the like are illustrated; as squalene synthase inhibitors, SDZ-268-198, BMS-188494, A-87049, RPR-101821, ZD-9720, RPR-107393, ER-27856, TAK-475 or the like are illustrated; as nicotinic acid derivatives, nicotinic acid, nicotinamide, nicomol, niceritrol, acipimox, nicorandil or the like are illustrated; as bile acid sequestrants, colestyramine, colestilan, colesevelam hydrochloride, GT-102-279 or the like are illustrated; as sodium/bile acid cotransporter inhibitors, 264W94, S-8921, SD-5613 or the like are illustrated; and as cholesterol ester transfer protein inhibitors, PNU-107368E, SC-795, JTT-705, CP-529414 or the like are illustrated. These drugs, probcol, microsomal trigylceride transfer protein inhibitors, lipoxygenase inhibitors and low-density lipoprotein receptor enhancers are preferably used for hyperlipidemia, hypercholesterolemia, hypertriglyceridemia or lipidmetabolism disorder.

As appetite suppressants, monoamine reuptake inhibitors, serotonin reuptake inhibitors, serotonin releasing stimulants, serotonin agonists (especially $5HT_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine-and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone receptor antagonists, agouti-related protein inhibitors and orexin receptor antagonists are illustrated. Concretely, as monoamine reuptake inhibitors, mazindol or the like are illustrated; as serotonin reuptake inhibitors, dexfenfluramine hydrochloride, fenfluramine, sibutramine hydrochloride, fluvoxamine maleate, sertraline hydrochloride or the like are illustrated; as serotonin agonists, inotriptan, (+)-norfenfluramine or the like are illustrated; as noradrenaline reuptake inhibitors, bupropion, GW-320659 or the like are illustrated; as noradrenaline releasing stimulants, rolipram, YM-992 or the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex or the like are illustrated; as dopamine agonists, ER-230, doprexin, bromocriptine mesylate or the like are illustrated; as cannabinoid receptor antagonists, rimonabant or the like are illustrated; as $\gamma$-aminobutyric acid receptor antagonists, topiramate or the like are illustrated; as $H_3$-histamine antagonists, GT-2394 or the like are illustrated; as leptin, leptin analogues or leptin receptor agonists, LY-355101 or the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 or the like are illustrated; and as neuropeptide Y antagonists, SR-120819-A, PD-160170, NGD-95-1, BIBP-3226, 1229-U-91, CGP-71683, BIBO-3304, CP-671906-01, J-115814 or the like are illustrated. Appetite suppressants are used preferably for diabetes, impaired glucose tolerance, diabetic complications, obesity, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril or the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril or the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 or the like are illustrated. Angiotensin II receptor antagonists are preferably used for diabetic complications or hypertension.

As endothelin-converting enzyme inhibitors, CGS-31447, CGS-35066, SM-19712 or the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride or the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride or the like are illustrated; as vasodilating antihypertensive agents, indapamide, todralazine hydrochloride, hydralazine hydrochloride, cadralazine, budralazine or the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin or the like are illustrated; as centrally acting antihypertensive agents, reserpine or the like are illustrated; and as $\alpha_2$-adrenoceptor agonists, clonidine hydrochloride, methyldopa, CHF-1035, guanabenz acetate, guanfacine hydrochloride, moxonidine, lofexidine, talipexole hydrochloride or the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin or the like are illustrated. Antiplatelets agents are preferably used for atherosclerosis or congestive heart failure.

As uric acid synthesis inhibitors, allopurinol, oxypurinol or the like are illustrated; as uricosuric agents, benzbromarone, probenecid or the like are illustrated; and as urinary alkalinizers, sodium hydrogen carbonate, potassium citrate, sodium citrate or the like are illustrated. These drugs are preferably used for hyperuricemia or gout.

In case of uses in combination with a compound of the present invention, for example, in the use for diabetes, the combination with at least one member of the group consisting of an insulin sensitivity enhancer, a glucose absorption inhibitor, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a glucose absorption inhibitor, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a glucose absorption inhibitor, a biguanide, an insulin secretion enhancer, a SGLT2 inhibitor and an insulin or insulin analogue is most preferable. Similarly, in the use for diabetic complications, the combination with at least one member of the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, cathartics, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, in the use for obesity, the combination with at least one member of the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a glucose absorption inhibitor, a SGLT2 inhibitor, a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered. The pharmaceutical compositions of the present invention also include sustained release formulation including gastrointestinal muco adhesive formulation (e.g., International publications Nos. WO99/10010, WO99/26606, and Japanese patent publication No. 2001-2567).

These pharmaceutical compositions can be prepared by admixing with or by diluting and dissolving with an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with conventional methods. In case of the uses of the compound of the present invention in combination with other drug(s), they can be prepared by formulating each active ingredient together or individually in a similar manner as defined above.

When the pharmaceutical compositions of the present invention are employed in the practical treatment, the dosage of a compound represented by the above general formula (I), a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the uses of the compound of the present invention in combination with other drug(s), the dosage of the compound of the present invention can be decreased, depending on the dosage of the drug(s).

EXAMPLES

The present invention is further illustrated in more detail by way of the following Reference Examples, Examples and Test Examples. However, the present invention is not limited thereto.

Reference Example 1

2-Bromo-6-fluorobenzaldehyde

To a solution of diisopropylamine (2.65 mL) in tetrahydrofuran (30 mL) was added n-butyllithium (2.44 mol/L n-hexane solution, 7.03 mL) at −78° C. under an argon atmosphere, and the mixture was stirred at the same temperature for 5 minutes. To the reaction mixture was added 3-bromofluorobenzene (3 g), and the mixture was stirred at the same temperature for 1 hour. To the reaction mixture was added N,N-dimethylformamide (1.45 mL), and the mixture was stirred at the same temperature for 10 minutes, then a saturated ammonium chloride aqueous solution was added to the reaction mixture, and the mixture was stirred under ice-cooling for 5 minutes. The mixture was poured into water, and the mixture was extracted with diethyl ether. The extract washed with water and brine and dried over anhydrous magnesium sulfate, and the solvent was removed under reduced pressure to give the title compound (3.43 g).

$^1$H-NMR (CDCl$_3$) δ ppm:
7.1-7.2 (1H, m), 7.35-7.45 (1H, m), 7.45-7.55 (1H, m), 10.36 (1H, s)

Reference Example 2

4-Bromobenzo[b]thiophene

To a suspension of sodium hydride (55%, 1.11 g) in dimethyl sulfoxide (20 mL) was added methyl thioglycolate (1.53 mL) at room temperature, and the mixture was stirred for 15 minutes. A solution of 2-bromo-6-fluorobenzaldehyde (3.43 g) in dimethyl sulfoxide (4 mL) was added to the reaction mixture, and the mixture was stirred at room temperature for 5 minutes. The reaction mixture was poured into water with ice and precipitated crystalline solid was collected by filtration, washed with water and dried under reduced pressure to give 2-methoxycarbonyl-4-bromobenzo-[b]thiophene (1.52 g). This material was suspended in a mixed solvent of methanol (20 mL) and water (10 mL) and sodium hydroxide (0.91 g) was added to the suspension. The mixture was stirred for at 50° C. for 5 hours. The reaction mixture was cooled with ice bath, and the reaction mixture was acidified by adding 2 mol/L hydrochloric acid. The precipitated crystalline solid was collected by filtration, washed with water and dried under reduced pressure to give 2-carboxybenzo[b]thiophene (1.27 g). To this material were added copper powder (0.42 g) and quinoline (10 mL), and the mixture was stirred at 190° C. for 1 hour. After the reaction mixture was cooled to room temperature, 2 mol/L hydrochloric acid (40 mL) and ethyl acetate (20 mL) were added to the reaction mixture, and the mixture was stirred for 15 minutes. Insoluble material in the mixture was removed by filtration, and the organic layer of the filtrate was separated. The aqueous layer of filtrate was extracted with ethyl acetate. The organic layers were combined, and the combined organic layer washed with 2 mol/L hydrochloric acid, water and brine and dried over anhydrous magnesium sulfate, and the solvent was removed under reduced pressure. The residue was purified by column chromatography on silica gel (eluent: n-hexane) to give the title compound (0.55 g).
¹H-NMR (CDCl₃) δ ppm:
7.15-7.25 (1H, m), 7.45-7.6 (3H, m), 7.82 (1H, d, J=8.2 Hz)

Reference Example 3

7-Bromobenzo[b]thiophene

To a mixture of 2-bromothiophenol (5 g) and 2-bromomethyl-1,3-dioxolane (2.98 mL) in N,N-dimethylformamide (50 mL) was added potassium carbonate (5.48 g) at room temperature, and the mixture was stirred overnight. The reaction mixture was poured into water, and the mixture was extracted with diethyl ether. The extract washed with water, 1 mol/L sodium hydroxide aqueous solution, water and brine successively, and dried over anhydrous magnesium sulfate, and the solvent was removed under reduced pressure to give (2-bromophenylthiomethyl)-1,3-dioxolane (7.25 g). To a mixture of poly phosphoric acid (20 g) and chlorobenzene (40 mL) was added a solution of (2-bromophenylthiomethyl)-1,3-dioxolene (7.25 g) in chlorobenzene (20 mL), and the mixture was refluxed for 8 hours. The reaction mixture was cooled to room temperature and supernatant solution was collected by decantation. Toluene was added to the residue, and the supernatant was collected by decantation after the mixture was stirred. The supernatant was combined and concentrated under reduced pressure. The residue was dissolved in ethyl acetate, and the solution washed with a saturated sodium hydrogencarbonate aqueous solution, water and brine and dried over anhydrous magnesium sulfate, and the solvent was removed under reduced pressure. The residue was purified by column chromatography on silica gel (eluent: n-hexane) to give the title compound (2.27 g).
¹H-NMR (CDCl₃) δ ppm:
7.25 (1H, t, J=7.8 Hz), 7.44 (1H, d, J=5.6 Hz), 7.45-7.55 (2H, m), 7.77 (1H, d, J=7.8 Hz)

Reference Example 4

4-[(E)-2-Phenylvinyl]benzo[b]thiophene

A mixture of 4-bromobenzo[b]thiophene (0.55 g), styrene (0.89 mL), triethylamine (1.81 mL), palladium(II) acetate (59 mg) and tris(2-methylphenyl)phosphine (0.16 g) in acetonitrile (10 mL) was refluxed overnight under an argon atmosphere. The reaction mixture was diluted with diethyl ether and an insoluble material was removed by filtration. The filtrate washed with 1 mol/L hydrochloric acid, water and brine successively, and dried over anhydrous magnesium sulfate, and the solvent was removed under reduced pressure. The residue was purified by column chromatography on silica gel (eluent: n-hexane-n-hexane/ethyl acetate=5/1) to give the title compound (0.56 g).
¹H-NMR (CDCl₃) δ ppm:
7.2-7.45 (6H, m), 7.51 (1H, d, J=5.5 Hz), 7.55-7.7 (4H, m), 7.81 (1H, d, J=7.8 Hz)

Reference Example 5

7-[(E)-2-Phenylvinyl]benzo[b]thiophene

The title compound was prepared in a similar manner to that described in Reference Example 4 using 7-bromobenzo[b]thiophene instead of 4-bromobenzo[b]thiophene.

¹H-NMR (CDCl₃) δ ppm:
7.25-7.45 (7H, m), 7.5 (1H, d, J=5.7 Hz), 7.55-7.65 (3H, m), 7.77 (1H, dd, J=7.9 Hz, 1.1 Hz)

Reference Example 6

4-(2-Phenylethyl)benzo[b]thiophene

To a solution of 4-[(E)-2-phenylvinyl]benzo[b]thiophene (0.56 g) and triethyl amine (2.63 mL) in tetrahydrofuran (25 mL) was added 2,4,6-triisopropylbenzenesulfonylhydrazide (5 g), and the mixture was refluxed overnight under an argon atmosphere. After the reaction mixture was cooled to room temperature, 2 mol/L hydrochloric acid was added to the mixture, and the mixture was stirred for 10 minutes. The mixture was poured into water, and the mixture was extracted with diethyl ether. The extract was washed with water and brine and dried over anhydrous magnesium sulfate, and the solvent was removed under reduced pressure. The residue was purified by column chromatography on silica gel (eluent: n-hexane) to give a mixture of the starting material and the title compound (0.43 g). This mixture was dissolved in triethylamine (2.04 g) and tetrahydrofuran (18 mL), and 2,4,6-triisopropylbenzenesulfonylhydrazide (3.28 g) was added to the solution, and the mixture was refluxed overnight under an argon atmosphere. The reaction mixture was cooled to room temperature and 2 mol/L hydrochloric acid was added to the mixture, and the mixture was stirred for 10 minutes. The mixture was poured into water, and the mixture was extracted with diethyl ether. The extract washed with water and brine and dried over anhydrous magnesium sulfate, and the solvent was removed under reduced pressure. The residue was purified by column chromatography on silica gel (eluent: n-hexane) to give the title compound (0.4 g).
¹H-NMR (CDCl₃) δ ppm:
3.0-3.05 (2H, m), 3.2-3.3 (2H, m), 7.1-7.35 (7H, m), 7.4-7.5 (2H, m), 7.75 (1H, d, J=8.0 Hz)

Reference Example 7

7-(2-Phenylethyl)benzo[b]thiophene

The title compound was prepared in a similar manner to that described in Reference Example 6 using 7-[(E)-2-phenylvinyl]benzo[b]thiophene instead of 4-[(E)-2-phenylvinyl]-benzo[b]thiophene.
¹H-NMR (CDCl₃) δ ppm:
3.05-3.15 (2H, m), 3.15-3.25 (2H, m), 7.1-7.35 (7H, m), 7.38 (1H, d, J=5.4 Hz), 7.44 (1H, d, J=5.4 Hz), 7.7 (1H, d, J=7.9 Hz)

Reference Example 8

2-(2,3,4,6-Tetra-O-benzyl-β-D-glucopyranosyl)-4-(2-phenylethyl)benzo[b]thiophene To a solution of 4-(2-phenylethyl)benzo[b]thiophene (0.4 g) in tetrahydrofuran (15 mL) was added n-butyllithium (2.44 mol/L n-hexane solution, 0.69 mL) at −78° C. under an argon atmosphere, and the mixture was stirred at the same temperature for 30 minutes. To the mixture was added a solution of 2,3,4,6-tetra-O-benzyl-D-glucono-1,5-lactone (0.82 g) in tetrahydrofuran (3 mL), and the mixture was stirred under ice-cooling for 10 minutes. The reaction mixture was poured into a saturated ammonium chloride aqueous solution, and the mixture was extracted with diethylether. The extract washed with water and brine and dried over anhydrous magnesium sulfate, and the solvent was removed under reduced pressure. The residue was purified by column chromatography on silica gel (eluent: n-hexane/ethyl acetate=4/1) to give 2,3,4,6-tetra-O-benzyl-1-[4-(2-phenylethyl)benzo[b]-thiophene-2-yl]-D-glucopyranose (1.02 g). This material was dissolved in acetonitrile (13 mL) and triethylsilane (0.42 mL) was added to the solution. Boron trifluoride diethylether complex (0.18 mL) was added to the solution at −20° C., and the mixture was stirred at room temperature for 1 hour. A saturated potassium carbonate aqueous solution was added to the reaction mixture, and the mixture was extracted with diethyl ether. The extract washed with water and brine and dried over anhydrous magnesium sulfate, and the solvent was removed under reduced pressure. The residue was purified by column chromatography on silica gel (eluent: n-hexane/ethyl acetate=8/1) to give the title compound (0.58 g).

$^1$H-NMR (CDCl$_3$) δ ppm:

2.9-3.05 (2H, m), 3.1-3.25 (2H, m), 3.6-3.7 (2H, m), 3.75-3.9 (4H, m), 4.11 (1H, d, J=10.4 Hz), 4.55-4.75 (5H, m), 4.88 (1H, d, J=10.7 Hz), 4.92 (1H, d, J=11.0 Hz), 4.96 (1H, d, J=11.0 Hz), 6.9-7.0 (2H, m), 7.05-7.4 (25H, m), 7.47 (1H, s), 7.7 (1H, d, J=8.1 Hz)

Reference Example 9

2-(2,3,4,6-Tetra-O-benzyl-β-D-glucopyranosyl)-7-(2-phenylethyl)benzo[b]thiophene The title compound was prepared in a similar manner to that described in Reference Example 8 using 7-(2-phenylethyl)benzo[b]thiophene instead of 4-(2-phenylethyl)benzo[b]thiophene.

$^1$H-NMR (CDCl$_3$) δ ppm:

3.0-3.2 (4H, m), 3.6-3.7 (2H, m), 3.75-3.9 (4H, m), 4.11 (1H, d, J=10.3 Hz), 4.5-4.75 (5H, m), 4.87 (1H, d, J=10.7 Hz), 4.92 (1H, d, J=11.0 Hz), 4.97 (1H, d, J=11.0 Hz), 6.95-7.0 (2H, m), 7.1-7.45 (26H, m), 7.62 (1H, d, J=7.8 Hz)

Example 1

2-(β-D-Glucopyranosyl)-4-(2-phenylethyl)benzo[b]thiophene

To a solution of 2-(2,3,4,6-tetra-O-benzyl-β-D-glucopyranosyl)-4-(2-phenylethyl)benzo[b]thiophene (0.58 g) and ethanethiol (1.13 mL) in dichloromethane (10 mL) was added boron trifluoride diethyl ether complex (1.43 mL) at room temperature, and the mixture was stirred for 3 hours. A saturated potassium carbonate aqueous solution was added to the reaction mixture, and the mixture was extracted with ethyl acetate. The extract washed with brine and dried over anhydrous magnesium sulfate, and the solvent was removed under reduced pressure. The residue was purified by column chromatography on silica gel (eluent: dichloromethane/methanol=10/1) to give the title compound (94 mg).

$^1$H-NMR (CD$_3$OD) δ ppm:

2.95-3.05 (2H, m), 3.15-3.25 (2H, m), 3.35-3.55 (4H, m), 3.72 (1H, dd, J=12.1 Hz, 6.0 Hz), 3.92 (1H, dd, J=12.1 Hz, 2.1 Hz), 4.55 (1H, d, J=8.8 Hz), 7.06 (1H, d, J=6.8 Hz), 7.1-7.3 (6H, m), 7.54 (1H, s), 7.66 (1H, d, J=8.3 Hz)

Example 2

2-(β-D-Glucopyranosyl)-7-(2-phenylethyl)benzo[b]thiophene

The title compound was prepared in a similar manner to that described in Example 1 using 2-(2,3,4,6-tetra-O-benzyl-β-D-glucopyranosyl)-7-(2-phenyletyl)benzo[b]thiophene instead of 2-(2,3,4,6-tetra-O-benzyl-β-D-glucopyranosyl)-4-(2-phenyletyl)benzo[b]thiophene.

$^1$H-NMR (CD$_3$OD) δ ppm:

3.0-3.1 (2H, m), 3.1-3.2 (2H, m), 3.35-3.55 (4H, m), 3.73 (1H, dd, J=12.1 Hz, 5.8 Hz), 3.93 (1H, dd, J=12.1 Hz, 2.0 Hz), 4.54 (1H, d, J=8.6 Hz), 7.06 (1H, d, J=6.5 Hz), 7.1-7.3 (6H, m), 7.41 (1H, s), 7.55-7.65 (1H, m)

Example 3

Process 1

Benzo[b]thiophen-7-yl-p-tolylmethanol

A Grignard reagent was prepared using 7-bromobenzo-[b]thiophene (1.0 g), magnesium (0.13 g), a catalytic amount of iodine and tetrahydrofuran (3 mL) according to the general method. To the Grignard reagent solution was added a solution of 4-methylbenzaldehyde (0.62 g) in tetrahydrofuran (5 mL) at 0° C. under an argon atmosphere. The reaction mixture was stirred at room temperature overnight and a saturated ammonium chloride aqueous solution was added to the mixture. The mixture was extracted with diethyl ether, and the organic layer washed with brine and dried over anhydrous magnesium sulfate. The solvent was removed under reduced pressure, and the residue was purified by column chromatography on aminopropylated silica gel (eluent: tetrahydrofuran). Further purification by column chromatography on silica gel (eluent; n-hexane/ethyl acetate=6/1) gave the title compound (0.68 g) as yellow oil.

$^1$H-NMR (CDCl$_3$) δ ppm:

2.32 (3H, s), 2.38 (1H, d, J=3.6 Hz), 6.11 (1H, d, J=3.4 Hz), 7.10-7.20 (2H, m), 7.30-7.45 (5H, m), 7.45-7.50 (1H, m), 7.70-7.80 (1H, m)

Process 2

7-(4-Methylbenzyl)benzo[b]thiophene

To a suspension of sodium iodide (2.0 g) in acetonitrile was added chlorotrimethylsilane (1.5 g) at room temperature. After the mixture was stirred at room temperature for 15 minutes, benzo[b]thiophen-7-yl-p-tolylmethanol (0.68 g) was added to the mixture, and the mixture was stirred at room temperature for 15 minutes. The reaction mixture was poured into water, and the mixture was extracted with hexane. The organic layer washed with water and brine and dried over anhydrous magnesium sulfate. The solvent was removed under reduced pressure, and the residue was purified by column chromatography on silica gel (eluent: n-hexane) to give the title compound (0.57 g) as colorless oil.

$^1$HMR (CDCl$_3$) δ ppm:

2.31 (3H, s), 4.20 (2H, s), 7.05-7.14 (3H, m), 7.14-7.20 (2H, m), 7.25-7.45 (3H, m), 7.65-7.75 (1H, m)

Process 3

2,3,4,6-Tetra-O-benzyl-1-[7-(4-methylbenzyl)benzo[b]thiophen-2-yl]-D-glucopyranose To a solution of 7-(4-methylbenzyl)benzo[b]thiophene (0.57 g) in tetrahydrofuran (10 mL) was added n-butyllithium (2.71 mol/L tetrahydrofuran solution, 0.88 mL) at −78° C. under an argon atmosphere. The mixture was stirred at the same temperature for 30 minutes and a solution of 2,3,4,6-tetra-O-benzyl-D-glucono-1,5-lactone (1.2 g) in tetrahydrofuran (5 mL) was added to the mixture. The reaction mixture was warmed to 0° C. and stirred for 10 minutes. The reaction mixture was poured into a saturated ammonium chloride aqueous solution, and the mixture was extracted with diethyl ether. The organic layer washed with brine and dried over anhydrous magnesium sulfate. The solvent was removed under reduced pressure, and the residue was purified by column chromatography on silica gel (eluent: n-hexane/ethyl acetate=4/1) to give the title compound (1.2 g).

Process 4

2-(2,3,4,6-Tetra-O-benzyl-β-D-glucopyranosyl)-7-(4-methylbenzyl)benzo[b]thiophene To a solution of 2,3,4,6-tetra-O-benzyl-1-[7-(4-methylbenzyl)benzo[b]thiophen-2-yl]-D-glucopyranose (1.2 g) and triethylsilane (0.49 mL), in acetonitrile (15 μL) was added boron trifluoride diethyl ether complex (2.0 mL) at −20° C., and the mixture was stirred for 1 hour. A saturated potassium carbonate aqueous solution was added to the mixture, and the mixture was extracted with diethyl ether. The organic layer washed with water and brine and dried over anhydrous magnesium sulfate. The solvent was removed under reduced pressure, and the residue was purified by column chromatography on silica gel (eluent: n-hexane/ethyl acetate=6/1) to give the title compound (0.95 g).

$^1$H-NMR (CDCl$_3$) δ ppm: 2.28 (3H, s), 3.55-3.70 (2H, m), 3.75-3.85 (4H, m), 4.09 (1H, d, J=10.5 Hz), 4.15-4.20 (2H, m), 4.52 (1H, d, J=10.4 Hz), 4.56-4.62 (2H, m), 4.62-4.72 (2H, m), 6.90-7.00 (2H, m), 7.00-7.40 (25H, m), 7.55-7.65 (1H, m)

Process 5

2-(β-D-Glucopyranosyl)-7-(4-methylbenzyl)benzo[b]thiophene

To a solution of 2-(2,3,4,6-tetra-O-benzyl-β-D-glucopyranosyl)-7-(4-methylbenzyl)benzo[b]thiophene (0.95 g) and ethanethiol (1.8 mL) in dichloromethane (15 mL) was added boron trifluoride diethyl ether complex (2.1 mL) at room temperature. The reaction mixture was stirred at room temperature for 3 hours, and a saturated potassium carbonate aqueous solution was added to the mixture. The mixture was extracted with ethyl acetate. The organic layer washed with brine and dried over anhydrous magnesium sulfate. The solvent was removed under reduced pressure, and the residue was purified by column chromatography on silica gel (eluent: dichloromethane/methanol=10/1) to give the title compound (0.16 g).

$^1$H-NMR (CD$_3$OD) δ ppm: 2.27 (3H, s), 3.30-3.50 (4H, m), 3.69 (1H, dd, J=5.9, 12.1 Hz), 3.90 (1H, dd, J=2.0, 12.1 Hz), 4.10-4.15 (2H, m), 4.50 (1H, d, J=9.0 Hz), 7.00-7.15 (5H, m), 7.25-7.35 (1H, m), 7.35-7.40 (1H, m), 7.55-7.70 (1H, m)

Example 4-Example 11

The compounds described in Table 1 or 2 were prepared in a similar manner to that described in Example 3 using corresponding starting materials.

TABLE 1

| Example number | Chemical structure | $^1$H-NMR (CD$_3$OD) δ ppm |
|---|---|---|
| Example 4 | 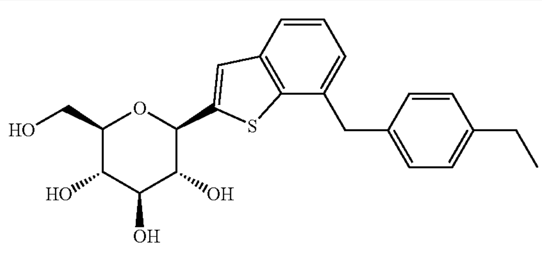 | 1.19 (3H, t, J=7.5 Hz), 2.58 (2H, q, J=7.5 Hz), 3.30-3.50 (4H, m), 3.69 (1H, dd, J=5.8, 12.1 Hz), 3.90 (1H, dd, J=1.9, 12.1 Hz), 4.10-4.20 (2H, m), 4.50 (1H, d, J=8.8 Hz), 7.00-7.20 (5H, m), 7.25-7.35 (1H, m), 7.35-7.45 (1H, m), 7.60-7.65 (1H, m) |
| Example 5 | 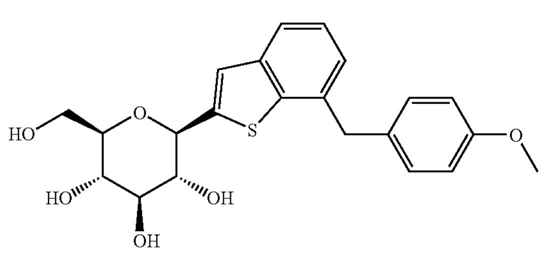 | 3.35-3.50 (4H, m), 3.69 (1H, dd, J=6.0, 12.1 Hz), 3.74 (3H, s), 3.90 (1H, dd, J=1.8, 12.1 Hz), 4.12 (2H, s), 4.50 (1H, d, J=9.2 Hz), 6.75-6.85 (2H, m), 7.05-7.20 (3H, m), 7.25-7.35 (1H, m), 7.35-7.45 (1H, m), 7.60-7.65 (1H, m) |

TABLE 1-continued

| Example number | Chemical structure | ¹H-NMR (CD₃OD) δ ppm |
|---|---|---|
| Example 6 | 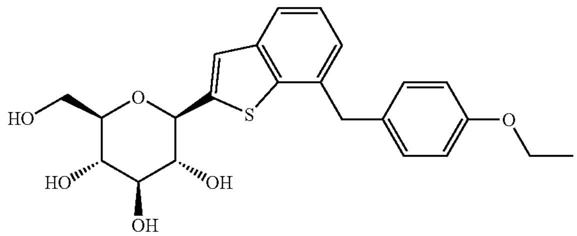 | 1.35 (3H, t, J=7.0 Hz), 3.30-3.50 (4H, m), 3.69 (1H, dd, J=5.8, 12.2 Hz), 3.90 (1H, dd, J=2.0, 12.2 Hz), 3.98 (2H, q, J=7.0 Hz), 4.11 (2H, s), 4.50 (1H, d, J=9.0 Hz), 6.75-6.85 (2H, m), 7.05-7.20 (3H, m), 7.25-7.35 (1H, m), 7.35-7.45 (1H, m), 7.60-7.65 (1H, m) |
| Example 7 | 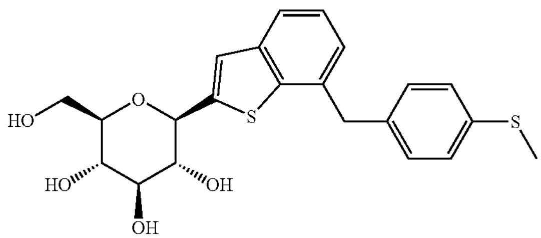 | 2.42 (3H, s), 3.30-3.50 (4H, m), 3.69 (1H, dd, J=5.9, 12.1 Hz), 3.90 (1H, dd, J=2.0, 12.1 Hz), 4.15 (2H, s), 4.50 (1H, d, J=9.2 Hz), 7.10-7.20 (5H, m), 7.25-7.35 (1H, m), 7.35-7.45 (1H, m), 7.60-7.70 (1H, m) |
| Example 8 | 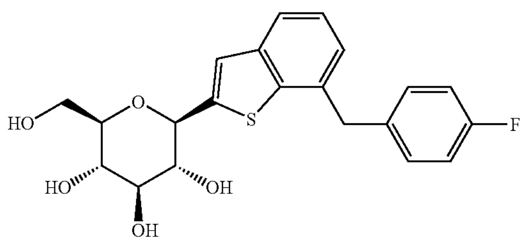 | 3.30-3.50 (4H, m), 3.69 (1H, dd, J=6.0, 12.0 Hz), 3.90 (1H, dd, J=2.0, 12.0 Hz), 4.17 (2H, s), 4.50 (1H, d, J=9.2 Hz), 6.90-7.00 (2H, m), 7.10-7.15 (1H, m), 7.20-7.35 (3H, m), 7.35-7.45 (1H, m), 7.60-7.70 (1H, m) |
| Example 9 | 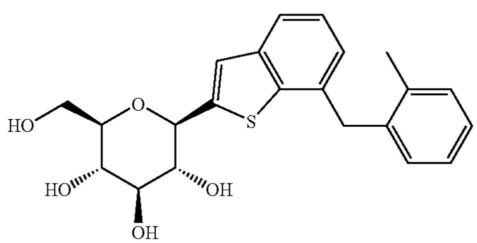 | 2.21 (3H, s), 3.30-3.55 (4H, m), 3.70 (1H, dd, J=6.0, 12.2 Hz), 3.91 (1H, dd, J=2.0, 12.2 Hz), 4.17 (2H, s), 4.52 (1H, d, J=9.3 Hz), 6.80-6.85 (1H, m), 7.00-7.30 (5H, m), 7.35-7.45 (1H, m), 7.60-7.65 (1H, m) |

TABLE 2

| Example number | Chemical structure | ¹H-NMR (CD₃OD) δ ppm |
|---|---|---|
| Example 10 | 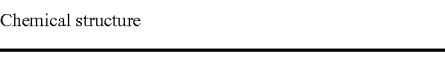 | 2.26 (3H, s), 3.30-3.50 (4H, m), 3.69 (1H, dd, J=6.0, 12.0 Hz), 3.90 (1H, dd, J=2.2, 12.0 Hz), 4.14 (2H, s), 4.50 (1H, d, J=9.1 Hz), 6.95-7.15 (5H, m), 7.25-7.35 (1H, m), 7.35-7.45 (1H, m), 7.60-7.65 (1H, m) |

TABLE 2-continued

| Example number | Chemical structure | $^1$H-NMR (CD$_3$OD) δ ppm |
|---|---|---|
| Example 11 | 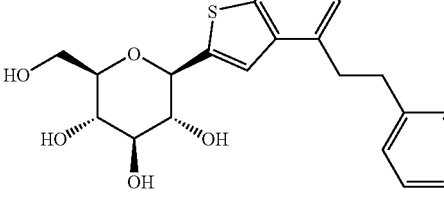 | 3.30-3.50 (4H, m), 3.70 (1H, dd, J=5.9, 12.0 Hz), 3.90 (1H, dd, J=2.2, 12.0 Hz), 4.12 (2H, s), 4.50 (1H, d, J=9.3 Hz), 7.10-7.17 (1H, m), 7.18-7.27 (4H, m), 7.18-7.35 (1H, m), 7.36-7.45 (1H, m) |

Example 12-Example 16

The compounds described in Table 3 or 4 were prepared in a similar manner to that described in Example 1 using corresponding starting materials.

TABLE 3

| Example number | Chemical structure | $^1$H-NMR (CD$_3$OD) δ ppm |
|---|---|---|
| Example 12 | 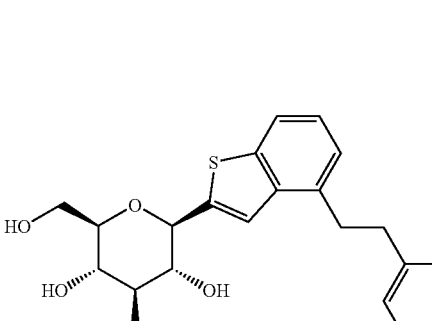 | 2.80-2.95 (2H, m), 3.10-3.20 (2H, m), 3.30-3.55 (4H, m), 3.72 (1H, dd, J=5.7, 12.1 Hz), 3.92 (1H, dd, J=2.1, 12.1 Hz), 4.54 (1H, d, J=9.2 Hz), 6.65-6.70 (2H, m), 6.95-7.02 (2H, m), 7.03-7.08 (1H, m), 7.15-7.20 (1H, m), 7.45-7.55 (1H, m), 7.60-7.70 (1H, m) |
| Example 13 | 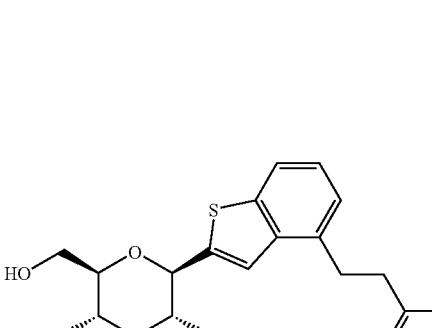 | 2.80-3.00 (2H, m), 3.10-3.25 (2H, m), 3.30-3.55 (4H, m), 3.72 (1H, dd, J=6.0, 11.8 Hz), 3.75 (3H, s), 3.92 (1H, dd, J=1.9, 11.8 Hz), 4.55 (1H, d, J=9.7 Hz), 6.75-6.85 (2H, m), 7.00-7.12 (3H, m), 7.14-7.20 (1H, m), 7.51 (1H, s), 7.65 (1H, d, J=8.5 Hz) |
| Example 14 | 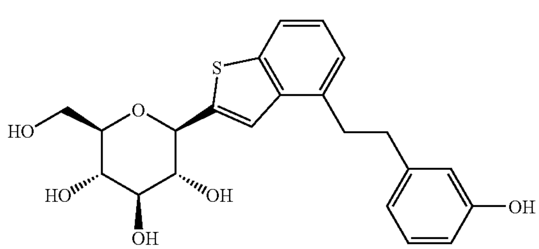 | 2.85-2.95 (2H, m), 3.10-3.25 (2H, m), 3.30-3.55 (4H, m), 3.72 (1H, dd, J=6.0, 12.1 Hz), 3.92 (1H, dd, J=2.3, 12.1 Hz), 4.55 (1H, d, J=8.9 Hz), 6.55-6.70 (3H, m), 7.00-7.10 (2H, m), 7.15-7.25 (1H, m), 7.52 (1H, s), 7.66 (1H, d, J=7.7 Hz) |

TABLE 4

| Example number | Chemical structure | ¹H-NMR (CD₃OD) δ ppm |
|---|---|---|
| Example 15 | 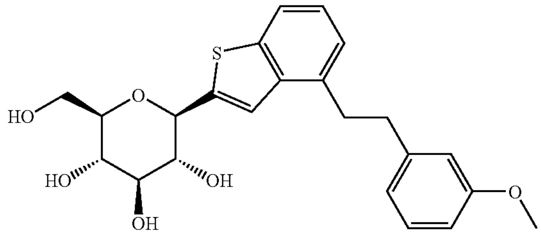 | 2.90-3.05 (2H, m), 3.15-3.25 (2H, m), 3.30-3.55 (4H, m), 3.72 (1H, dd, J=6.1, 11.9 Hz), 3.72 (3H, s), 3.92 (1H, dd, J= 2.4, 11.9 Hz), 4.55 (1H, d, J=8.9 Hz), 6.65-6.75 (2H, m), 6.75-6.80 (1H, m), 7.00-7.10 (1H, m), 7.10-7.25 (2H, m), 7.52 (1H, s), 7.66 (1H, d, J=8.4 Hz) |
| Example 16 | 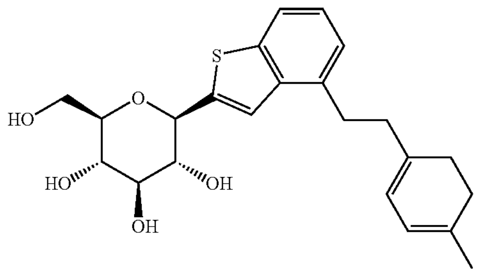 | 2.28 (3H, s), 2.85-3.00 (2H, m), 3.10-3.25 (2H, m), 3.35-3.55 (4H, m), 3.72 (1H, dd, J=6.0, 12.1 Hz), 3.92 (1H, dd, J=2.3, 12.1 Hz), 4.55 (1H, d, J=8.8 Hz), 7.00-7.10 (5H, m), 7.10-7.25 (1H, m), 7.52 (1H, m), 7.65 (1H, d, J=7.9 Hz) |

The compounds described in Table 5 can be prepared in a similar manner to that described in the above Examples or Reference Examples.

TABLE 5

TABLE 5-continued

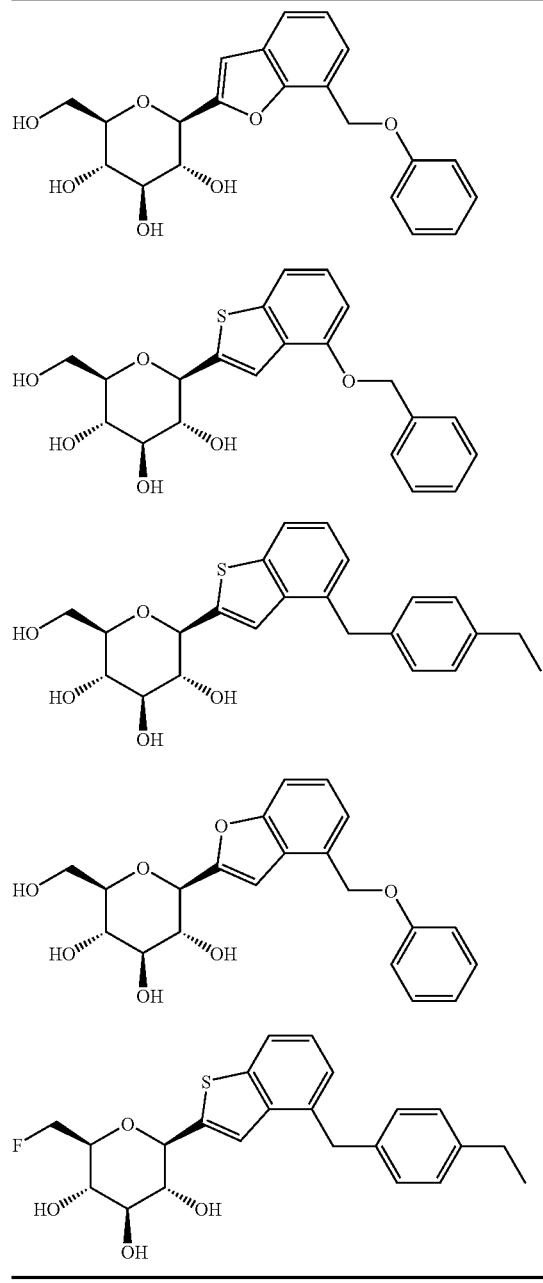

Test Example 1

Assay for Inhibitory Effects on Human SGLT1 Activity

1) Cloning and Construction of the Vector Expressing Human SGLT1

The cDNA library was prepared for PCR amplification by reverse transcription from total RNA deprived from human small intestine (Ori gene) using oligo-dT as a primer. Using this cDNA library as a template, the DNA fragment coding 1 to 2005 bp of human SGLT1 (ACCESSION: M24847), which was reported by Hediger et al., was amplified by PCR method and inserted into the multi-cloning site of pcDNA3.1 (−) (Invitrogen). The DNA sequence inserted was perfectly matched to the previously reported sequence.

2) Establishment of Cell Line Stably Expressing Human SGLT1

The expression vector of human SGLT1 was digested by Sca I into a linear DNA. The linear DNA was transfected into CHO-K1 cells by means of lipofection (Effectene Transfection Reagent: QIAGEN). Neomycin resistant cell lines were selected by culture in the medium containing G418 (1 mg/mL, LIFE TECHNOLOGIES), and then the activity against the uptake of methyl-α-D-glucopyranoside was measured by the method described below. The cell line, which showed the greatest uptake activity, was selected and designated as CS1-5-11D. CS1-5-11D cells were cultured in the presence of G418 at 200 μg/mL.

3) Measurement of the Inhibitory Activity Against the Uptake of Methyl-α-D-glucopyranoside (α-MG)

CS1-5-11D cells were seeded into a 96-well culture plate at a density of $3\times10^4$ cells/well and cultured for 2 days, and were used in the uptake assay. A mixture of non-labeled (Sigma) and $^{14}C$-labeled α-MG (Amersham Pharmacia Biotech) was added to the uptake buffer (pH 7.4; containing 140 mM sodium chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris (hydroxymethyl)aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal uptake measurement buffer which contains 140 mM chorine chloride instead of sodium chloride was prepared. After removing the culture medium of CS1-5-11D cells, 180 μL of the pre-treatment buffer (the basal uptake buffer without (α-MG) was added to each well and incubated at 37° C. for 10 minutes. After repeating the same treatment, the pre-treatment buffer was removed. To each well was added 75 μL of the measurement buffer or the basal uptake buffer was added and incubated at 37° C. for 1 hour. After removing the measurement buffer, cells were washed twice with 180 μL per well of the washing buffer (the basal uptake buffer containing 10 mM non-labeled α-MG). The cells were solubilized by 75 μL per well of 0.2 mol/L sodium hydroxide. The cell lysates were transferred into PicoPlates (Packard), and then added 150 μL of MicroScint-40 (Packard) and mixed. Radioactivity was measured by means of micro-scintillation counter Top-Count (Packard). One hundred % was set to the difference between the uptake in the control group and the basal uptake, and the uptake of methyl α-D-glucopyranoside at each drug concentration were calculated. The drug concentration, at which 50% uptake of methyl α-D-glucopyranoside was inhibited ($IC_{50}$ value), was calculated using logit plot. The results are shown in Table 6.

TABLE 6

| Test compound | $IC_{50}$ value (nM) |
|---|---|
| Example 1 | 220 |

Test Example 2

Assay for Inhibitory Effects on Human SGLT2 Activity

1) Cloning and Construction of the Vector Expressing Human SGLT2

The cDNA library was prepared for PCR amplification by reverse transcription from total RNA deprived from human kidney (Ori gene) using oligo-dT as a primer. Using this cDNA library as a template, the DNA fragment coding 2 to 2039 bp of human SGLT2 (ACCESSION: M95549, M95299), which was reported by R. G. Wells et al., was amplified by PCR method and inserted into the multi-cloning site of pcDNA3.1 (−) (Invitrogen). The DNA sequence inserted was perfectly matched to the previously reported sequence.

2) Establishment of Cell Line Stably Expressing Human SGLT2

The expression vector of human SGLT2 was digested by Sca I into a linear DNA. The linear DNA was transfected into CHO-K1 cells by means of lipofection (Effectene Transfection Reagent: QIAGEN). Neomycin resistant cell lines were selected by culture in the medium containing G418 (1 mg/mL, LIFE TECHNOLOGIES), and then the activity against the uptake of methyl-α-D-glucopyranoside was measured by the method described below. The cell line, which showed the greatest uptake activity, was selected and designated as CS2-5E. CS2-5E cells were cultured in the presence of G418 at 200 μg/mL.

3) Measurement of the Inhibitory Activity Against the Uptake of Methyl-α-D-glucopyranoside (α-MG)

CS2-5E cells were seeded into a 96-well culture plate at a density of $3 \times 10^4$ cells/well and cultured for 2 days, and were used in the uptake assay. A mixture of non-labeled (Sigma) and $^{14}$C-labeled α-MG (Amersham Pharmacia Biotech) was added to the uptake buffer (pH 7.4; containing 140 mM sodium chloride, 2 mM potassium chloride, 1 mM calcium chloride, 1 mM magnesium chloride, mM 2-[4-(2-hydroxyethyl)-1-piperazinyl]ethane sulfonic acid and 5 mM tris(hydroxymethyl)aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal uptake measurement buffer which contains 140 mM chorine chloride instead of sodium chloride was prepared. After removing the culture medium of CS1-5-11D cells, 180 μL of the pre-treatment buffer (the basal uptake buffer without α-MG) was added to each well and incubated at 37° C. for 10 minutes. After repeating the same treatment, the pre-treatment buffer was removed. To each well was added 75 μL of the measurement buffer or the basal uptake buffer was added and incubated at 37° C. for 1 hour. After removing the measurement buffer, cells were washed twice with 180 μL per well of the washing buffer (the basal uptake buffer containing 10 mM non-labeled α-MG). The cells were solubilized by 75 μL per well of 0.2 mol/L sodium hydroxide. The cell lysates were transferred into PicoPlates (Packard), and then added 150 μL of MicroScint-40 (Packard) and mixed. Radioactivity was measured by means of micro-scintillation counter Top-Count (Packard). One hundred % was set to the difference between the uptake in the control group and the basal uptake, and the uptake of methyl α-D-glucopyranoside at each drug concentration were calculated. The drug concentration, at which 50% uptake of methyl α-D-glucopyranoside was inhibited ($IC_{50}$ value), was calculated using logit plot. The results are shown in Table 7.

TABLE 7

| Test compound | $IC_{50}$ value (nM) |
|---|---|
| Example 1 | 58 |
| Example 2 | 130 |
| Example 3 | 2.0 |

INDUSTRIAL APPLICABILITY

The fused heterocyclic derivatives represented by the above general formula (I) of the present invention, pharmaceutically acceptable salts thereof and prodrugs thereof exert an inhibitory activity in human SGLT and can suppress increase of blood glucose level or lower blood glucose level by inhibiting absorption of carbohydrate such as glucose at the small intestine or by inhibiting reabsorption of glucose at the kidney. Therefore, the present invention can provide excellent agents for the prevention or treatment of a disease associated with hyperglycemia such as diabetes, postprandial hyperglycemia, impaired glucose tolerance, diabetic complications, obesity or the like.

The invention claimed is:

1. A fused heterocyclic derivative represented by the following general formula (I):

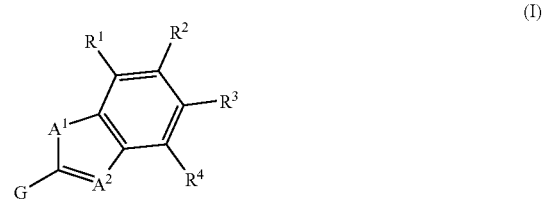

(I)

wherein
one of $R^1$ and $R^4$ represents a group represented by the general formula:

(S)

in the formula $R^5$ and $R^6$ independently represent a hydrogen atom, a hydroxy group, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{2-6}$ alkenylthio group, a halo($C_{1-6}$ alkyl) group, a halo($C_{1-6}$ alkoxy) group, a halo($C_{1-6}$ alkylthio) group, a hydroxy($C_{1-6}$ alkyl) group, a hydroxy($C_{2-6}$ alkenyl) group, a hydroxy($C_{1-6}$ alkoxy) group, a hydroxy ($C_{1-6}$ alkylthio) group, a carboxy group, a carboxy($C_{1-6}$ alkyl) group, a carboxy($C_{2-6}$ alkenyl) group, a carboxy ($C_{1-6}$ alkoxy) group, a carboxy($C_{1-6}$ alkylthio) group, a $C_{2-7}$ alkoxycarbonyl group, a alkoxycarbonyl($C_{1-6}$ alkyl) group, a $C_{2-7}$ alkoxycarbonyl($C_{2-6}$ alkenyl) group, a $C_{2-7}$ alkoxycarbonyl($C_{1-6}$ alkoxy) group, a $C_{2-7}$ alkoxycarbonyl($C_{1-6}$ alkylthio) group, a $C_{1-6}$ alkylsulfinyl group, a $C_{1-6}$ alkylsulfonyl group, —U—V—W—N($R^7$)—Z, or any of the following substituents (i) to (xxviii) which may have 1 to 3 substituents selected from the later identified substituent group α on the ring;
(i) a $C_{6-10}$ aryl group, (ii) $C_{6-10}$ aryl-O—, (iii) $C_{6-10}$ aryl-S—, (iv) a $C_{6-10}$ aryl($C_{1-6}$ alkyl) group, (v) a $C_{6-10}$ aryl ($C_{1-6}$ alkoxy) group, (vi) a $C_{6-10}$ aryl($C_{1-6}$ alkylthio) group, (vii) a heteroaryl group, (viii) heteroaryl-O—, (ix) heteroaryl-S—, (x) a heteroaryl($C_{1-6}$ alkyl) group, (xi) a heteroaryl($C_{1-6}$ alkoxy) group, (xii) a heteroaryl ($C_{1-6}$ alkylthio) group, (xiii) a $C_{3-7}$ cycloalkyl group, (xiv) $C_{3-7}$ cycloalkyl-O—, (xv) $C_{3-7}$ cycloalkyl-S—, (xvi) a $C_{3-7}$ cycloalkyl($C_{1-6}$ alkyl) group, (xvii) a $C_{3-7}$ cycloalkyl($C_{1-6}$ alkoxy) group, (xviii) a $C_{3-7}$ cycloalkyl ($C_{1-6}$ alkylthio) group, (xix) a heterocycloalkyl group, (xx) heterocycloalkyl-O—, (xxi) heterocycloalkyl-S—, (xxii) a heterocycloalkyl($C_{1-6}$ alkyl) group, (xxiii) a heterocycloalkyl($C_{1-6}$ alkoxy) group, (xxiv) a heterocycloalkyl($C_{1-6}$ alkylthio) group, (xxv) an aromatic cyclic amino group, (xxvi) an aromatic cyclic amino($C_{1-6}$ alkyl) group or (xxvii) an aromatic cyclic amino($C_{1-6}$ alkoxy) group, (xxviii) an aromatic cyclic amino($C_{1-6}$ alkylthio) group, U represents —O—, —S— or a single bond and with the proviso that at least one of V and W is not a single bond when U is —O— or —S—);

V represents a $C_{1-6}$ alkylene group which may have a hydroxy group, a $C_{2-6}$ alkenylene group or a single bond;

W represents —CO—, —SO$_2$—, —C(=NH)— or a single bond;

Z independently represents a hydrogen atom, a $C_{2-7}$ alkoxycarbonyl group, a $C_{6-10}$ aryl($C_{2-7}$ alkoxycarbonyl) group, a formyl group, —$R^A$, —$COR^B$, —$SO_2R^B$, —$CON(R^C)R^D$, —$CSN(R^C)R^D$, —$SO_2NHR^A$ or —$C(=NR^E)N(R^F)R^G$;

$R^7$, $R^A$, $R^C$ and $R^D$ independently represent a hydrogen atom, a $C_{1-6}$ alkyl group which may have 1 to 5 substituents selected from the later identified substituent group β, or any of the following substituents (xxix) to (xxxii) which may have 1 to 3 substituents selected from the later identified substituent group α;
(xxix) a $C_{6-10}$ aryl group, (xxx) a heteroaryl group, (xxxi) a $C_{3-7}$ cycloalkyl group or (xxxii) a heterocycloalkyl group or Z and $R^7$ bind together with the neighboring nitrogen atom to form an aliphatic cyclic amino group which may have 1 to 3 substituents selected from the later identified substituent group α;

or $R^C$ and $R^D$ bind together with the neighboring nitrogen atom to form an aliphatic cyclic amino group which may have 1 to 3 substituents selected from the later identified substituent group α;

$R^B$ represents a $C_{2-7}$ alkoxycarbonyl group, a $C_{1-6}$ alkylsulfonylamino group, a $C_{6-10}$ arylsulfonylamino group, a $C_{1-6}$ alkyl group which may have 1 to 5 substituents selected from the later identified substituent group β or any of the following substituents (xxxiii) to (xxxvi) which may have 1 to 3 substituents selected from the later identified substituent group α;
(xxxiii) a $C_{6-10}$ aryl group, (xxxiv) a heteroaryl group, (xxxv) a $C_{3-7}$ cycloalkyl group or (xxxvi) a heterocycloalkyl group, $R^E$, $R^F$ and $R^G$ independently represent a hydrogen atom, a cyano group, a carbamoyl group, a $C_{2-7}$ acyl group, a $C_{2-7}$ alkoxycarbonyl group, a $C_{6-10}$ aryl($C_{2-7}$ alkoxycarbonyl) group, a nitro group, a $C_{1-6}$ alkylsulfonyl group, a sulfamide group, a carbamimidoyl group or a $C_{1-6}$ alkyl group which may have 1 to 5 substituents selected from the later identified substituent group β;

or $R^E$ and $R^F$ bind together to form an ethylene group;

or $R^F$ and $R^G$ bind together with the neighboring nitrogen atom to form an aliphatic cyclic amino group which may have any substituent selected from the later identified substituent group α;

Q represents —$C_{1-6}$ alkylene-, —$C_{2-6}$ alkenylene-, —$C_{2-6}$ alkynylene-, —$C_{1-6}$ alkylene-O—, —$C_{1-6}$ alkylene-S—, —O—$C_{1-6}$ alkylene-, —S—$C_{1-6}$ alkylene-, —$C_{1-6}$ alkylene-O—$C_{1-6}$ alkylene-, —$C_{1-6}$ alkylene-S—$C_{1-6}$ alkylene-, —$CON(R^8)$—, —$N(R^8)CO$—, —$C_{1-6}$ alkylene-$CON(R^8)$— or —$CON(R^8)$—$C_{1-6}$ alkylene-;

$R^8$ represents a hydrogen atom or a $C_{1-6}$ alkyl group;

ring A represents a $C_{6-10}$ aryl group or a heteroaryl group, and the other one of $R^1$ and $R^4$ represents a hydrogen atom, a hydroxy group, an amino group, a halogen atom, a $C_{1-6}$ alkyl group, a $C_{1-6}$ alkoxy group, a cyano group, a carboxy group, a $C_{2-7}$ alkoxycarbonyl group, a carbamoyl group, a mono or di($C_{1-6}$ alkyl)amino group, a halo($C_{1-6}$ alkyl) group, a hydroxy($C_{1-6}$ alkyl) group, a cyano($C_{1-6}$ alkyl) group, a carboxy($C_{1-6}$ alkyl) group, a $C_{2-7}$ alkoxycarbonyl($C_{1-6}$ alkyl) group, a carbamoyl($C_{1-6}$ alkyl) group, an amino($C_{1-6}$ alkyl) group, a mono or di($C_{1-6}$ alkyl)amino($C_{1-6}$ alkyl) group, a halo($C_{1-6}$ alkoxy) group, a hydroxy($C_{1-6}$ alkoxy) group, a carboxy($C_{1-6}$ alkoxy) group, a $C_{2-7}$ alkoxycarbonyl($C_{1-6}$ alkoxy) group, a carbamoyl($C_{1-6}$ alkoxy) group, an amino($C_{1-6}$ alkoxy) group, a mono or di($C_{1-6}$ alkyl)amino($C_{1-6}$ alkoxy) group, a $C_{3-7}$ cycloalkyl group, a $C_{3-7}$ cycloalkyloxy group, a $C_{3-7}$ cycloalkyl($C_{1-6}$ alkyl) group, or $C_{3-7}$ cycloalkyl($C_{1-6}$ alkoxy) group;

$R^2$ and $R^3$ independently represent a hydrogen atom, a hydroxy group, an amino group, a halogen atom, a $C_{1-6}$ alkyl group, a $C_{1-6}$ alkoxy group, a cyano group, a carboxy group, a $C_{2-7}$ alkoxycarbonyl group, a carbamoyl group, a mono or di($C_{1-6}$ alkyl)amino group, a halo($C_{1-6}$ alkyl) group, a hydroxy($C_{1-6}$ alkyl) group, a cyano($C_{1-6}$ alkyl) group, a carboxy($C_{1-6}$ alkyl) group, a $C_{2-7}$ alkoxycarbonyl($C_{1-6}$ alkyl) group, a carbamoyl($C_{1-6}$ alkyl) group, an amino($C_{1-6}$ alkyl) group, a mono or di($C_{1-6}$ alkyl)amino($C_{1-6}$ alkyl) group, a halo($C_{1-6}$ alkoxy) group, a hydroxy($C_{1-6}$ alkoxy) group, a carboxy($C_{1-6}$ alkoxy) group, a $C_{2-7}$ alkoxycarbonyl($C_{1-6}$ alkoxy) group, a carbamoyl($C_{1-6}$ alkoxy) group, an amino($C_{1-6}$ alkoxy) group, a mono or di($C_{1-6}$ alkyl)amino($C_{1-6}$ alkoxy) group, a $C_{3-7}$ cycloalkyl group, a $C_{3-7}$ cycloalkyloxy group, a $C_{3-7}$ cycloalkyl($C_{1-6}$ alkyl) group, or $C_{3-7}$ cycloalkyl($C_{,1-6}$ alkoxy) group;

$A^1$ represents O, S or $NR^9$;

$A^2$ represents CH or N;

$R^9$ represents a hydrogen atom or a $C_{1-6}$ alkyl group;

G represents a group represented by a formula:

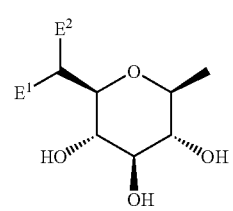

(G-1)

or a formula:

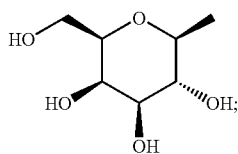

(G-2)

$E^1$ represents a hydrogen atom, a fluorine atom or a hydroxy group;

$E^2$ represents a hydrogen atom, a fluorine atom, a methyl group or a hydroxymethyl group;

substituent group α:

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy)group, a hydroxy($C_{1-6}$ alkyl) group, a $C_{2-7}$ alkoxycarbonyl($C_{1-6}$ alkyl) group, a hydroxy($C_{1-6}$ alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)] amino group, a $C_{1-6}$ alkylsulfonyl group, a $C_{1-6}$ alkylsulfonylamino group, a $C_{1-6}$ alkylsulfonylamino($C_{1-6}$ alkyl) group, a carboxy group, a $C_{2-7}$ alkoxycarbonyl group, a sulfamoyl group and —CON($R^H$)$R^I$ substituent group β:

a halogen atom, a hydroxy group, an amino group, a $C_{1-6}$ alkoxy group, a $C_{1-6}$ alkylthio group, a halo($C_{1-6}$ alkoxy) group, a halo($C_{1-6}$ alkylthio) group, a hydroxy($C_{1-6}$ alkoxy) group, a hydroxy($C_{1-6}$ alkylthio) group, an amino($C_{1-6}$ alkoxy) group, an amino($C_{1-6}$ alkylthio) group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di[hydroxy($C_{1-6}$ alkyl)]ureido group, a mono or di($C_{1-6}$ alkyl)sulfamide group, a mono or di[hydroxy($C_{1-6}$ alkyl)]-sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl ($C_{1-6}$ alkylsulfonylamino) group, a carboxy group, a $C_{2-7}$ alkoxycarbonyl group, —CON($R^H$)$R^I$, and any of the following substituents (xxxvii) to (xxxxviii) which may have 1 to 3 substituents selected from the above substituent group α;

(xxxvii) a $C_{6-10}$ aryl group, (xxxviii) $C_{6-10}$ aryl-O—, (xxxix) a $C_{6-10}$ aryl($C_{1-6}$ alkoxy) group, (xxxx) a $C_{6-10}$ aryl($C_{1-6}$ alkylthio) group, (xxxxi) a heteroaryl group, (xxxxii) heteroaryl-O—, (xxxxiii) a $C_{3-7}$ cycloalkyl group, (xxxxiv) $C_{3-7}$ cycloalkyl-O—, (xxxxv) a heterocyclo-alkyl group, (xxxxvi) heterocycloalkyl-O—, (xxxxvii) an aliphatic cyclic amino group or (xxxxviii) an aromatic cyclic amino group $R^H$ and $R^I$ independently represent a hydrogen atom or a $C_{1-6}$ alkyl group which may have 1 to 3 substituents selected from the later identified substituent group γ; or both of $R^H$ and $R^I$ bind together with the neighboring nitrogen atom to form an aliphatic cyclic amino group which may have 1 to 3 substituents selected from the later identified substituent group δ;

substituent group γ:

a halogen atom, a hydroxy group, an amino group, a $C_{1-6}$ alkoxy group, a halo($C_{1-6}$ alkoxy) group, a hydroxy($C_{1-6}$ alkoxy) group, an amino($C_{1-6}$ alkoxy) group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di[hydroxy($C_{1-6}$ alkyl)]ureido group, a mono or di($C_{1-6}$ alkyl)sulfamide group, a mono or di[hydroxy($C_{1-6}$ alkyl)]sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl($C_{1-6}$ alkylsulfonylamino) group, a carboxy group, a $C_{2-7}$ alkoxycarbonyl group, a sulfamoyl group and —CON($R^J$)$R^K$ substituent group δ:

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy) group, a hydroxy($C_{1-6}$ alkyl) group, a $C_{2-7}$ alkoxycarbonyl($C_{1-6}$ alkyl) group, a hydroxy($C_{1-6}$ alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)] amino group, a $C_{1-6}$ alkylsulfonyl group, a $C_{1-6}$ alkylsulfonylamino group, a $C_{1-6}$ alkylsulfonylamino($C_{1-6}$ alkyl) group, a carboxy group, a $C_{2-7}$ alkoxycarbonyl group, a sulfamoyl group and —CON($R^J$)$R^K$ $R^J$ and $R^K$ independently represent a hydrogen atom or a $C_{1-6}$ alkyl group which may have any 1 to 3 substituents selected from a hydroxy group, an amino group, a mono or di($C_{1-6}$ alkyl)amino group, a $C_{2-7}$ alkoxycarbonyl group and a carbamoyl group;

or both of $R^J$ and $R^K$ bind together with the neighboring nitrogen atom to form an aliphatic cyclic amino group which may have any 1 to 3 substituents selected from a hydroxy group, an amino group, a mono or di($C_{1-6}$ alkyl) amino group, a $C_{1-6}$ alkyl group, a hydroxy($C_{1-6}$ alkyl) group, a $C_{2-7}$ alkoxycarbonyl group, a $C_{2-7}$ alkoxycarbonyl($C_{1-6}$ alkyl) group and a carbamoyl group, or a pharmaceutically acceptable salt thereof.

2. A fused heterocyclic derivative as claimed in claim 1, wherein Q represents an ethylene group, or a pharmaceutically acceptable salt thereof.

3. A fused heterocyclic derivative as claimed in claim 1, wherein $R^5$ and $R^6$ independently represent a hydrogen atom, or a pharmaceutically acceptable salt thereof.

4. A fused heterocyclic derivative as claimed in claim 1, wherein the ring A represents a benzene ring or a pyridine ring, or a pharmaceutically acceptable salt thereof.

5. A fused heterocyclic derivative as claimed in claim 1, wherein G represents a group represented by the formula:

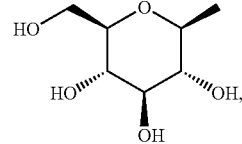

or a pharmaceutically acceptable salt thereof.

6. A pharmaceutical composition comprising as an active ingredient a fused heterocyclic derivative as claimed in claim 1, or a pharmaceutically acceptable salt thereof.

7. A human SGLT inhibitor comprising as an active ingredient a fused heterocyclic derivative as claimed in claim 1, or a pharmaceutically acceptable salt thereof.

8. A human SGLT inhibitor as claimed in claim 7, wherein the SGLT is SGLT1 and/or SGLT2.

9. A human SGLT inhibitor as claimed in claim 7, which is an agent for the treatment of a disease associated with hyperglycemia.

10. A human SGLT inhibitor as claimed in claim 9, wherein the disease associated with hyperglycemia is a disease selected from the group consisting of diabetes, impaired glucose tolerance, diabetic complications, obesity, hyperinsulinemia, hyperlipidemia, hypertriglyceridemia, lipid metabolism disorder, atherosclerosis, hypertension, and edema.

11. A pharmaceutical composition as claimed in claim 6, wherein the dosage form is sustained release formulation.

12. A human SGLT inhibitor as claimed in claim 7, wherein the dosage form is sustained release formulation.

13. A method for the inhibition of postprandial hyperglycemia, which comprises administering an effective amount of a fused heterocyclic derivative as claimed in claim 1, or a pharmaceutically acceptable salt thereof.

14. A method for the treatment of a disease associated with hyperglycemia, which comprises administering an effective amount of a fused heterocyclic derivative as claimed in claim 1, or a pharmaceutically acceptable salt thereof.

15. A method for the treatment as claimed in claim 14, wherein the disease associated with hyperglycemia is a disease selected from the group consisting of diabetes, impaired glucose tolerance, diabetic complications, obesity, hyperinsulinemia, hyperlipidemia, hypertriglyceridemia, lipid metabolism disorder, atherosclerosis, hypertension and edema.

16. A method for the inhibition of advancing impaired glucose tolerance into diabetes in a subject, which comprises administering an effective amount of a fused heterocyclic derivative as claimed in claim 1, or a pharmaceutically acceptable salt thereof.

* * * * *